(12) United States Patent
Frater et al.

(10) Patent No.: US 10,758,696 B2
(45) Date of Patent: Sep. 1, 2020

(54) MOUTH SEAL ASSEMBLY FOR NASAL MASK SYSTEM

(71) Applicant: ResMed Pty Ltd, Bella Vista, New South Wales (AU)

(72) Inventors: Robert Henry Frater, Sydney (AU); Gregory Robert Peake, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 628 days.

(21) Appl. No.: 15/601,182

(22) Filed: May 22, 2017

(65) Prior Publication Data

US 2017/0259021 A1 Sep. 14, 2017

Related U.S. Application Data

(62) Division of application No. 11/988,931, filed as application No. PCT/AU2006/001246 on Aug. 28, 2006, now abandoned.

(60) Provisional application No. 60/711,669, filed on Aug. 29, 2005.

(51) Int. Cl.
*A61M 16/06* (2006.01)
*A61M 16/04* (2006.01)
*A62B 9/06* (2006.01)

(52) U.S. Cl.
CPC ........ *A61M 16/06* (2013.01); *A61M 16/0493* (2014.02); *A61M 16/0611* (2014.02); *A61M 16/0638* (2014.02); *A61M 16/0683* (2013.01); *A61M 16/0694* (2014.02); *A61M 2210/0618* (2013.01); *A61M 2210/0625* (2013.01); *A62B 9/06* (2013.01)

(58) Field of Classification Search
CPC .. A61M 16/00; A61M 16/06; A61M 16/0488; A61M 16/0493; A61M 16/0605; A61M 16/0616; A61M 16/0622; A61M 2016/0661; A61M 16/208; A61M 16/209; A61M 16/0677
See application file for complete search history.

(56) References Cited

U.S. PATENT DOCUMENTS

D32,565 S  *  4/1900 Hooper .................. D24/191
746,869 A      12/1903 Moulton
(Continued)

FOREIGN PATENT DOCUMENTS

AU    2004/100928 A4    12/2004
EP      0 549 299 A2     6/1993
(Continued)

OTHER PUBLICATIONS

Apr. 27, 2010 Office Action issued in corresponding Chinese Application No. 200680032112.9.
(Continued)

*Primary Examiner* — Michael J Tsai
(74) *Attorney, Agent, or Firm* — Nixon & Vanderhye P.C.

(57) ABSTRACT

A mouth seal assembly for use with a nasal mask system includes a mouth seal adapted to form a seal with the patient's mouth. The mouth seal is substantially independent from a supply of pressurized air from the nasal mask system. An anti-asphyxia valve may be provided to either the mouth seal over the patient's lips or the nasal mask system. A strap arrangement may support the mouth seal in a desired position on the patient's face in use.

26 Claims, 20 Drawing Sheets

(56) References Cited

U.S. PATENT DOCUMENTS

| | | | | |
|---|---|---|---|---|
| 1,629,892 | A * | 5/1927 | Storms | A61F 5/56 128/848 |
| 1,873,160 | A | 2/1929 | Sturtevant | |
| 1,775,718 | A * | 9/1930 | Garvey | A61F 5/56 128/848 |
| 2,627,268 | A * | 2/1953 | Leppich | A61F 5/566 128/848 |
| 4,817,636 | A * | 4/1989 | Woods | A61F 5/56 128/848 |
| 5,462,050 | A * | 10/1995 | Dahlstrand | A61M 16/06 128/205.25 |
| 5,540,223 | A * | 7/1996 | Starr | A61M 16/06 128/205.25 |
| 5,560,354 | A | 10/1996 | Berthon-Jones et al. | |
| 5,918,598 | A | 7/1999 | Belfer et al. | |
| 6,012,455 | A * | 1/2000 | Goldstein | A61M 16/0488 128/204.18 |
| 6,076,526 | A * | 6/2000 | Abdelmessih | A61F 5/56 128/848 |
| 6,112,746 | A | 9/2000 | Kwok et al. | |
| 6,123,082 | A | 9/2000 | Berthon-Jones et al. | |
| 6,209,542 | B1 * | 4/2001 | Thornton | A61F 5/566 128/201.18 |
| 6,405,729 | B1 | 6/2002 | Thornton | |
| 6,470,886 | B1 | 10/2002 | Jestrabek-Hart | |
| 6,571,798 | B1 | 6/2003 | Thornton | |
| 6,789,543 | B2 | 9/2004 | Cannon | |
| 6,907,878 | B1 | 6/2005 | Resnick | |
| 7,021,312 | B2 * | 4/2006 | Cannon | A61M 16/0683 128/206.29 |
| 7,318,437 | B2 | 1/2008 | Gunaratnam et al. | |
| 7,500,480 | B2 * | 3/2009 | Matula, Jr. | A61M 16/06 128/200.24 |
| 2002/0069872 | A1 | 6/2002 | Gradon et al. | |
| 2003/0121520 | A1 * | 7/2003 | Parker | A61M 16/208 128/206.21 |
| 2003/0149387 | A1 * | 8/2003 | Barakat | A61F 5/56 602/45 |
| 2004/0065328 | A1 | 4/2004 | Amarasinghe et al. | |
| 2004/0079374 | A1 * | 4/2004 | Thornton | A61M 16/06 128/206.21 |
| 2004/0118406 | A1 | 6/2004 | Lithgow et al. | |
| 2005/0178392 | A1 * | 8/2005 | Tinsley | A61F 5/56 128/848 |
| 2005/0241644 | A1 | 11/2005 | Gunaratnam et al. | |
| 2007/0006879 | A1 * | 1/2007 | Thornton | A61M 16/06 128/203.29 |
| 2011/0315143 | A1 * | 12/2011 | Frater | A61M 16/0638 128/205.24 |
| 2014/0251335 | A1 * | 9/2014 | Black | A61M 16/0616 128/205.25 |
| 2017/0028162 | A1 * | 2/2017 | Leeflang | A61F 5/56 |
| 2018/0078726 | A1 * | 3/2018 | Barraclough | A61M 16/0816 |

FOREIGN PATENT DOCUMENTS

| | | |
|---|---|---|
| GB | 2 368 533 A1 | 5/2002 |
| WO | 98/26829 A1 | 6/1998 |
| WO | 99/061089 A1 | 12/1999 |
| WO | 2003/057293 A1 | 7/2003 |
| WO | 2005/063328 A1 | 7/2005 |

OTHER PUBLICATIONS

Aug. 1, 2012 Office Communication issued in European Application No. 06774875.6.
Aug. 20, 2015 Communication Pursuant to Article 94(3) EPC issued in European Application No. 12162717.8.
Aug. 31, 2012 Office Action issued in Chinese Application No. 200680032112.9 (with English translation).
Dec. 4, 2009 European Search Report issued in European Application No. 06774875.6.
Jan. 28, 2013 Office Action issued in Chinese Application No. 200680032112.9 (with English translation).
May 4, 2016 Communication Pursuant to Article 94(3) EPC issued in European Application No. 12162717.8.
May 6, 2015 Office Action issued in Chinese Application No. 2013104854302 (with English translation).
May 28, 2014 European Office Action issued in European Application No. 06774875.6.
Nov. 6, 2006 International Search Report issued in International Application No. PCT/AU2006/001246.
Nov. 12, 2012 Extended European Search Report issued in European Application No. 12162717.8.

* cited by examiner

MOUTH SEAL ASSEMBLY FOR NASAL MASK SYSTEM

CROSS-REFERENCE TO PRIORITY APPLICATION

This application is a divisional of U.S. application Ser. No. 11/988,931, filed Jan. 17, 2008, which is a U.S. national phase of International Application No. PCT/AU2006/001246, filed Aug. 28, 2006, which designated the U.S. and claims the benefit to U.S. Provisional Application No. 60/711,669, filed Aug. 29, 2005, the entire contents of each of which are hereby incorporated by reference.

FIELD OF THE INVENTION

The present invention relates to a mouth seal assembly for use with a nasal mask system for Non-invasive Positive Pressure Ventilation (NIPPV) and for continuous positive airway pressure (CPAP) therapy of sleep disordered breathing (SDB) conditions such as obstructive sleep apnea (OSA).

BACKGROUND OF THE INVENTION

Treatment of sleep disordered breathing (SDB), such as obstructive sleep apnea (OSA), by continuous positive airway pressure (CPAP) mask systems involves the continuous delivery of air (or other breathable gas) pressurized above atmospheric pressure to the airways of a human or other mammalian patient via a conduit and a mask. Typically, the mask fits over the nose and/or mouth of the patient. Pressurized air flows to the mask and to the airways of the patient via the nose and/or mouth. As the patient exhales, carbon dioxide gas may collect in the mask. A washout vent in the mask or conduit discharges the exhaled gas from the mask atmosphere.

When nasal mask systems are used, e.g., nasal masks or nozzle assemblies, some patients have a tendency for mouth leak. Alternatively, some patients may have a tendency for mouth breathing when using a nasal mask system. When air escapes through the patient's mouth, the patient does not obtain the full benefit of the delivered treatment pressure. Therefore, the effectiveness of CPAP therapy is diminished. In addition, mouth leak may result in noise, increased treatment pressure to compensate for the leak, increased load on the nasal passages, nasal obstruction, and/or runny nose, for example. The reduction of mouth leak and the prevention of mouth breathing encourage nasal breathing which may prove beneficial for the patient.

PCT Application No. PCT/AU2004/001832 and U.S. Pat. Nos. 1,873,160, 5,560,354, 6,123,082, and 6,571,798 disclose devices that attempt to reduce mouth leak.

SUMMARY OF THE INVENTION

One aspect of the invention relates to a mouth seal assembly for use with a nasal mask system that eliminates or at least minimizes mouth leak.

Another aspect of the invention relates to a mouth seal assembly for use with a nasal mask system that eliminates mouth breathing.

Another aspect of the invention relates to a mouth seal assembly for use with a nasal mask system. The mouth seal assembly includes a mouth seal adapted to form a seal with the patient's mouth. The mouth seal is substantially independent from a supply of pressurized air from the nasal mask system. An anti-asphyxia valve is provided to the mouth seal over the patient's lips.

Yet another aspect of the invention relates to a nasal mask system including a nasal mask structured to form a seal with the patient's nose and deliver a supply of pressurized air and a mouth seal assembly attached to the nasal mask. The mouth seal assembly includes a mouth seal adapted to form a seal with the patient's mouth. The mouth seal is substantially independent from the supply of pressurized air. An anti-asphyxia valve is provided to the mouth seal over the patient's lips.

Still another aspect of the invention relates to a mouth seal assembly for use with a nasal mask system. The mouth seal assembly includes a substantially rigid tube adapted to form a seal with the patient's lips. The tube is substantially independent from a supply of pressurized air from the nasal mask system. A strap arrangement supports the tube in a desired position on the patient's face in use.

Still another aspect of the invention relates to a nasal mask system including a nasal mask structured to form a seal with the patient's nose and deliver a supply of pressurized air and a mouth seal adapted to form a seal with the patient's mouth. The nasal mask includes a nasal assembly structured to sealingly communicate with nasal passages of the patient's nose in use and headgear provided to the nasal assembly to maintain the nasal assembly in a desired position on the patient's face. The mouth seal is substantially independent from the supply of pressurized air. The nasal assembly and/or headgear supports the mouth seal in position on the patient's face.

Still another aspect of the invention relates to a mouth seal assembly for use with a nasal mask system. The mouth seal assembly includes a mouth seal adapted to form a seal with the patient's mouth and a mount provided to the mouth seal and adapted to support the mouth seal on the nasal mask system. The mouth seal is substantially independent from a supply of pressurized air from the nasal mask system. The mouth seal is formed with foam to provide a foam seal or interface with the patient's mouth in use.

Still another aspect of the invention relates to a nasal mask system including a nasal mask structured to form a seal with the patient's nose and deliver a supply of pressurized air and a mouth seal assembly provided to the nasal mask. The mouth seal assembly includes a mouth seal adapted to form a seal with the patient's mouth and a mount adapted to support the mouth seal on the nasal mask. The mouth seal includes a bellows or gusset arrangement that provides the mouth seal with a sealing force onto the patient's mouth in use.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Embodiments of the invention are directed towards a mouth seal assembly for use with a nasal mask system that eliminates or at least minimizes mouth leak and/or mouth breathing. The mouth seal assembly may be retrofit to an existing nasal mask system, e.g., nasal mask, nozzle assembly, nasal assembly, nasal prongs, nasal pillows, nasal cannulae, nasal inserts, nozzles, etc, or the mouth seal assembly may be provided as original equipment along with a nasal mask system. The mouth seal assembly may or may not include an anti-asphyxia valve. Also, the mouth seal assembly may be supported by a strap arrangement and/or mount that is separate from and/or integrated with the nasal mask system.

While the mouth seal assembly is described as being used in conjunction with or as part of a nasal mask system, the mouth seal assembly may be adapted for use with other suitable breathing arrangements. That is, the breathing arrangements are merely exemplary, and aspects of the present invention may be applicable to other breathing arrangements, e.g., full-face masks.

1. First Embodiment of Mouth Seal Assembly

Figure 2:
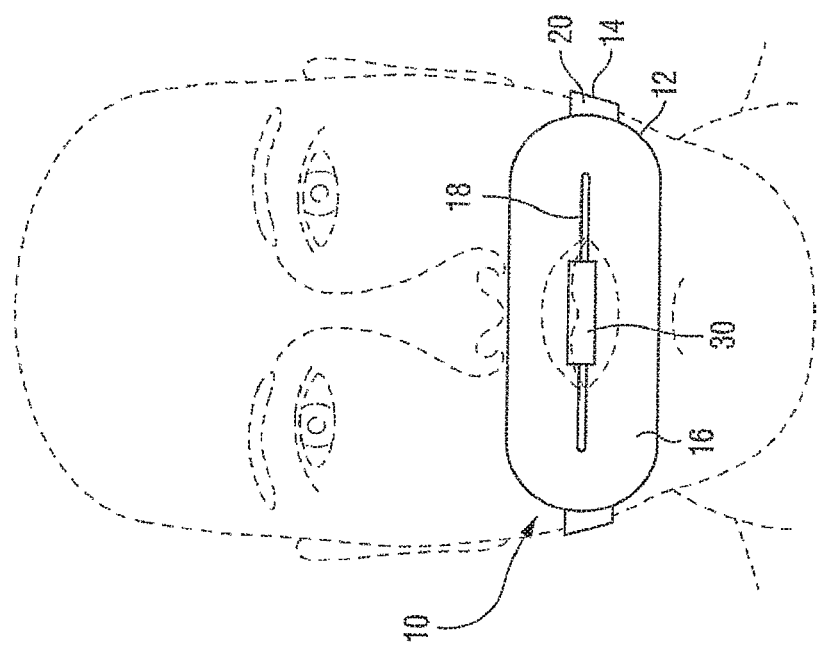
FIG. 2 is a front view of the mouth seal assembly shown in FIG. 1.
Figure 1:
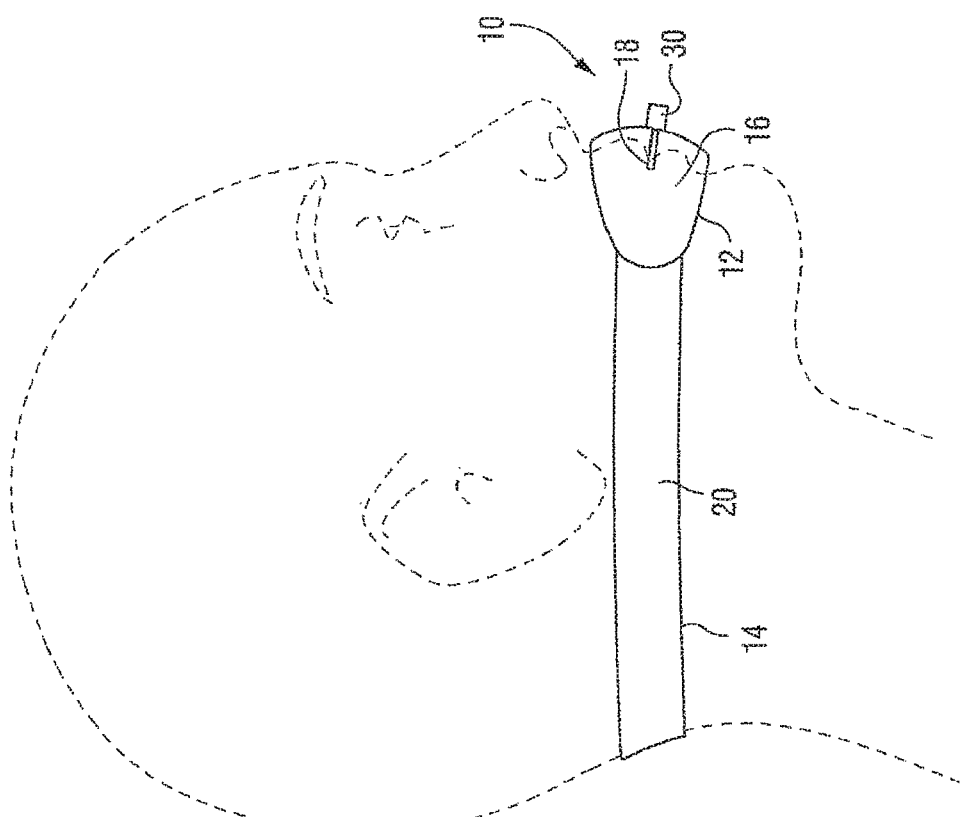
FIG. 1 is a side view of a mouth seal assembly according to an embodiment of the present invention.

FIGS. 1 and 2 illustrate a mouth seal assembly 10 according to an embodiment of the present invention. As illustrated, the mouth seal assembly 10 includes a mouth seal 12 adapted to form a seal with the patient's mouth and a strap arrangement 14 attached to the mouth seal 12 to maintain the mouth seal 12 in a desired position on the patient's face. The mouth seal assembly 10 is intended to be used in conjunction with or as a part of a nasal mask system that provides pressurized breathable gas to the patient's nose, e.g., nasal passages. In use, the mouth seal assembly 10 eliminates or at least minimizes mouth leak in order to enhance the effectiveness of therapy.

In the illustrated embodiment, the mouth seal 12 includes a flat strip of silicone 16 or similar flexible material. As illustrated, the mouth seal 12 includes a length and height sufficient to completely cover the patient's mouth. A small ridge 18 may be incorporated into the mouth seal 12 to assist location between the patient's lips. The mouth seal 12 is held against the patient's lips by the strap arrangement 14 which includes a strap 20 that extends around the back of the patient's neck. Ends of the strap 20 may be attached to the mouth seal 12 in any suitable manner, e.g., anchors, hook and loop fasteners, etc.

The mouth seal assembly 10 also includes an anti-asphyxia valve 30 that provides an air passage to the patient in the absence of pressure. The anti-asphyxia valve 30 is provided to the mouth seal 12 over the patient's lips to allow the patient to breathe in freely in the absence of pressure but prevent exhalation.

In an alternative embodiment, the mouth seal assembly 10 may be used without the anti-asphyxia valve 30. In this embodiment, the patient may open his/her mouth to breath when air pressure is not present, e.g., in the case of a power supply failure. This is possible since a seal is formed by air pressure causing the patient's lips to "bellow". Thus, the seal is only "activated" when air pressure is present.

The mouth seal assembly 10 differs from a mask in that it is independent from the supply of pressurized air. In use, when the patient has a tendency for mouth leak, the pressure inside the patient's mouth pushes the patient's lips against the mouth seal 12. Thus, the patient's lips conform to the mouth seal 12 due to the differential pressure between the patient's mouth and the outside of the mouth seal 12. This arrangement enables an effective mouth seal, thereby eliminating or at least minimizing the loss of therapy effectiveness resulting from mouth leak.

Figure 4:
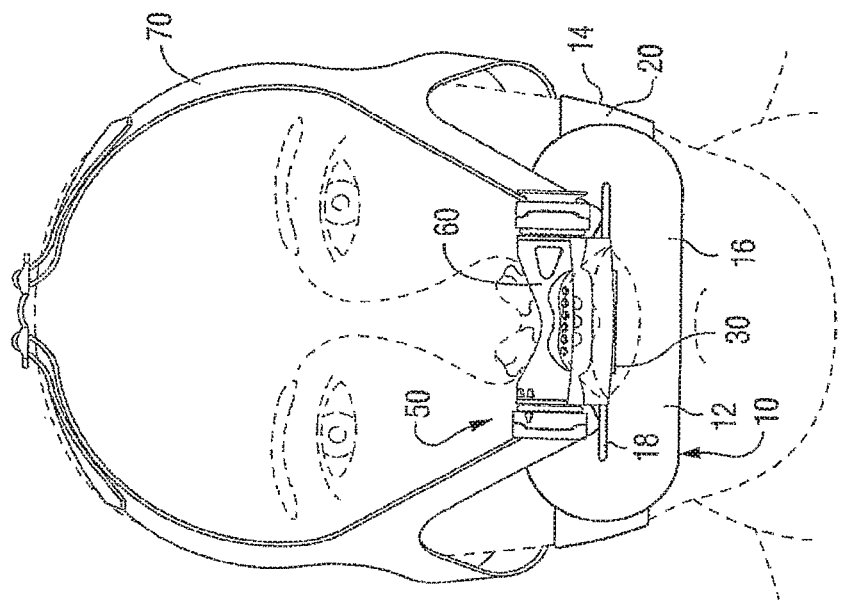
FIG. 4 is a front view of the mouth seal assembly and nasal mask system shown in FIG. 3.
Figure 3:
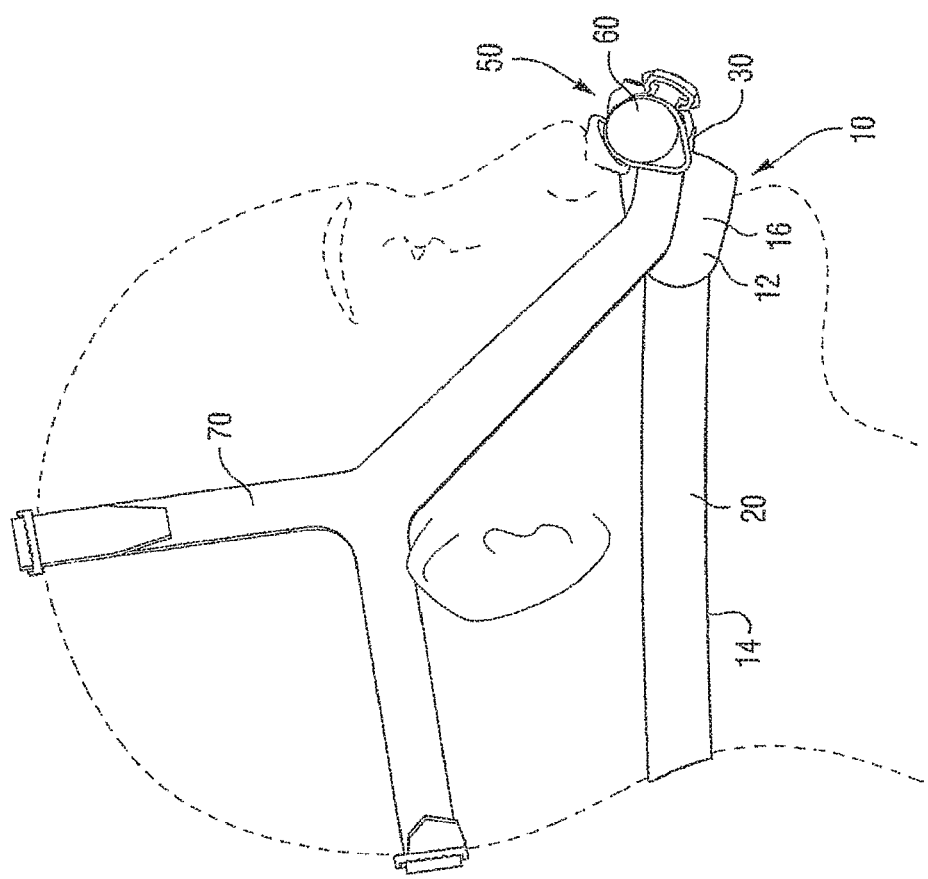
FIG. 3 is a side view of the mouth seal assembly shown in FIG. 1 being used in conjunction with a nasal mask system.

FIGS. 3 and 4 illustrate the mouth seal assembly 10 being used in conjunction with a nasal mask system. As illustrated, the nasal mask system includes a nasal mask 50 adapted to form a seal with the patient's nose, e.g., nasal passages. The nasal mask 50 includes a nasal assembly 60 structured to sealingly communicate with nasal passages of the patient's nose in use, and headgear 70 attached to the nasal assembly 60 to maintain the nasal assembly 60 in a desired position on the patient's face.

The illustrated nasal mask 50 is commercially sold under the name of SWIFT® by ResMed Ltd. Further details and embodiments of this nasal mask 50 are disclosed in U.S. patent application Ser. Nos. 10/781,929, filed Feb. 20, 2004, now U.S. Pat. No. 7,318,437, and Ser. No. 11/101,657, filed Apr. 8, 2005, now U.S. Pat. No. 7,942,150, the entireties of both being incorporated herein by reference. While the mouth seal assembly 10 is described as being used in conjunction with a nasal mask of the type described above, it may be implemented into other nasal masks. That is, the nasal mask 50 is merely exemplary, and the mouth seal assembly 10 may be used in conjunction with any suitable nasal mask, e.g., nasal assembly, nasal prongs, nasal pillows, nasal cannulae, nasal inserts, nozzles, etc.

In the illustrated embodiment, the mouth seal assembly 10 includes its own strap arrangement 14 to maintain the mouth seal 12 in a desired position. However, the headgear 70 of the nasal mask 50 may be modified to hold the mouth seal 12 in place. In this arrangement, a separate adjustment may be provided to adjust the position of the mouth seal 12. It is also possible that the mouth seal 12 may be maintained in position without straps. In an alternative embodiment, the mask may be modified to add support to the mouth seal.

2. Second Embodiment of Mouth Seal Assembly

Figure 6:
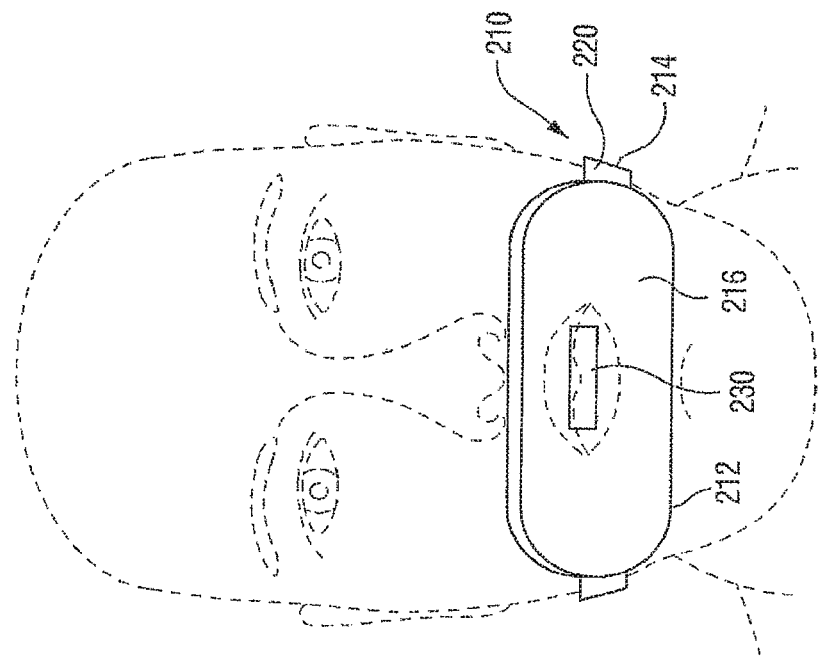
FIG. 6 is a front view of the mouth seal assembly shown in FIG. 5.
Figure 5:
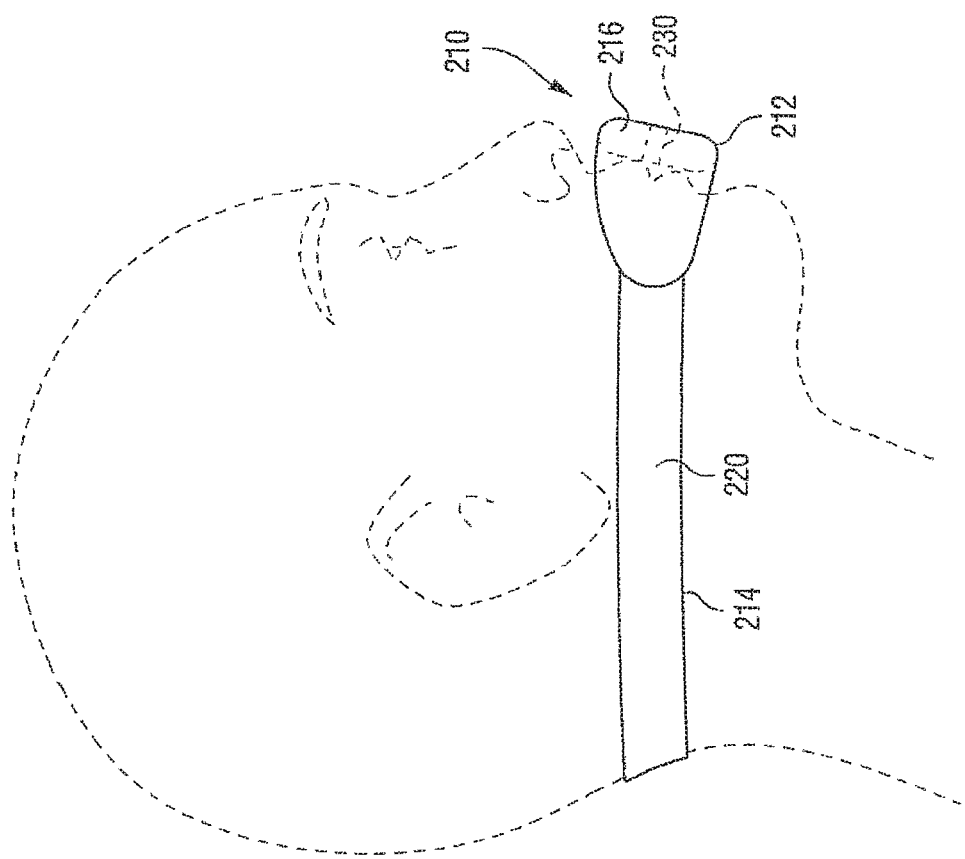
FIG. 5 is a side view of a mouth seal assembly according to another embodiment of the present invention.

FIGS. 5 and 6 illustrate a mouth seal assembly 210 according to another embodiment of the present invention. As illustrated, the mouth seal assembly 210 includes a mouth seal 212 adapted to form a seal with the patient's mouth and a strap arrangement 214 attached to the mouth seal 212 to maintain the mouth seal 212 in a desired position on the patient's face.

In the illustrated embodiment, the mouth seal 212 includes an inflated, gel-filled, or foam-filled balloon section 216. As illustrated, the mouth seal 212 includes a length and height sufficient to completely cover the patient's mouth. The mouth seal 212 is held against the patient's lips by the strap arrangement 214 which includes a strap 220 that extends around the back of the patient's neck. Ends of the strap 220 may be attached to the mouth seal 212 in any suitable manner, e.g., anchors, hook and loop fasteners, etc.

The mouth seal assembly 210 also includes an anti-asphyxia valve 230 that provides an air passage to the patient in the absence of pressure. The anti-asphyxia valve 230 is provided to the mouth seal 212 over the patient's lips to allow the patient to breathe in freely in the absence of pressure but prevent exhalation.

Similar to the mouth seal assembly 10 described above, the mouth seal assembly 210 is independent from the supply of pressurized air and the patient's lips conform to the mouth seal 212 due to the differential pressure between the patient's mouth and the outside of the mouth seal.

In an alternative embodiment, the mouth seal assembly 210 may be used without the anti-asphyxia valve 230. In this embodiment, the patient may open his/her mouth to breath when air pressure is not present, e.g., in the case of a power supply failure. This is possible since a seal is formed by air pressure causing the patient's lips to "bellow". Thus, the seal is only "activated" when air pressure is present.

In an embodiment, the mouth seal assembly 210 may include a small locating ridge such as that described above. In another embodiment, the balloon section 216 may be solid and shaped to fit the patient's lips.

3. Third Embodiment of Mouth Seal Assembly

Figure 7:
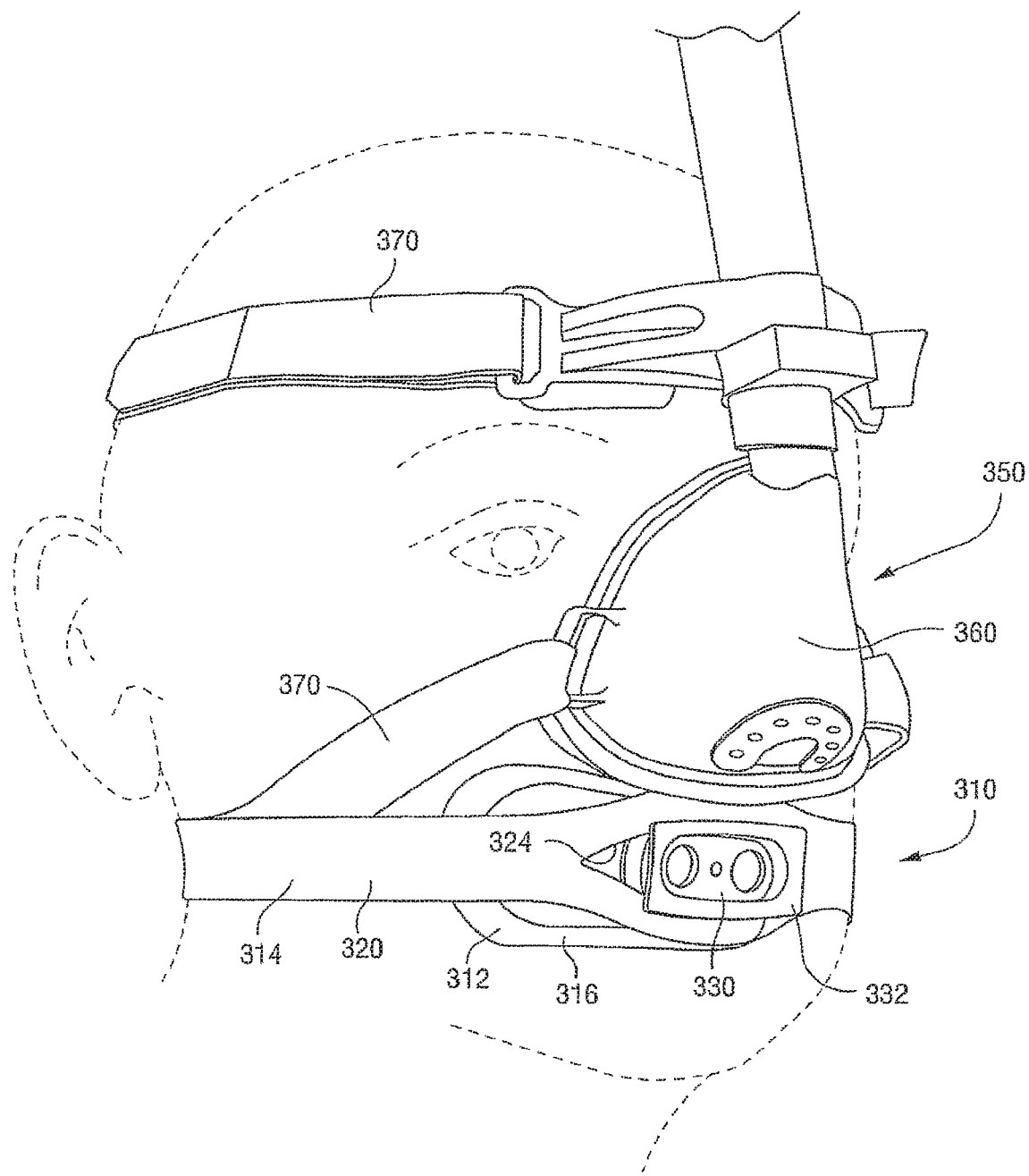
FIG. 7 is a perspective view of a mouth seal assembly according to another embodiment of the present invention, the mouth seal assembly being used in conjunction with a nasal mask system.
Figure 8:
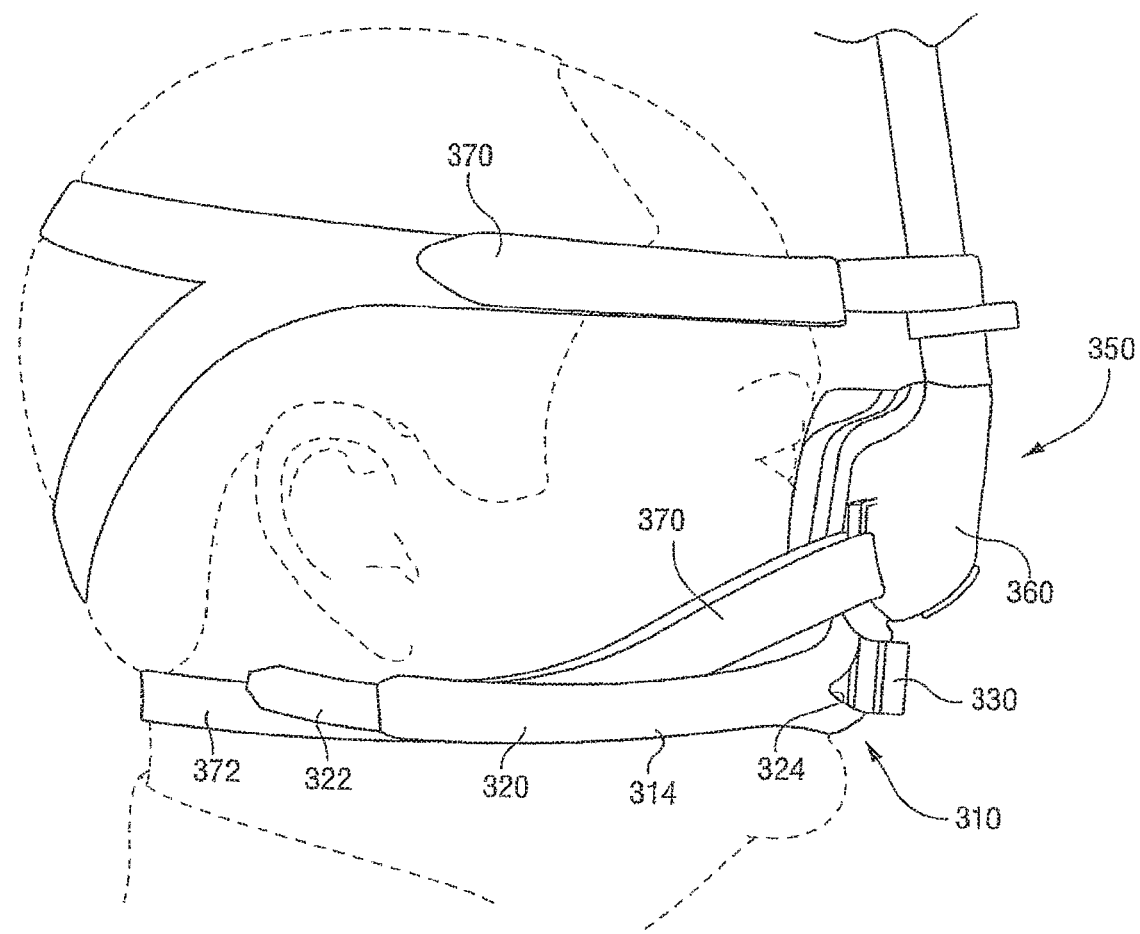
FIG. 8 is a side view of the mouth seal assembly and nasal mask system shown in FIG. 7.
Figure 9:
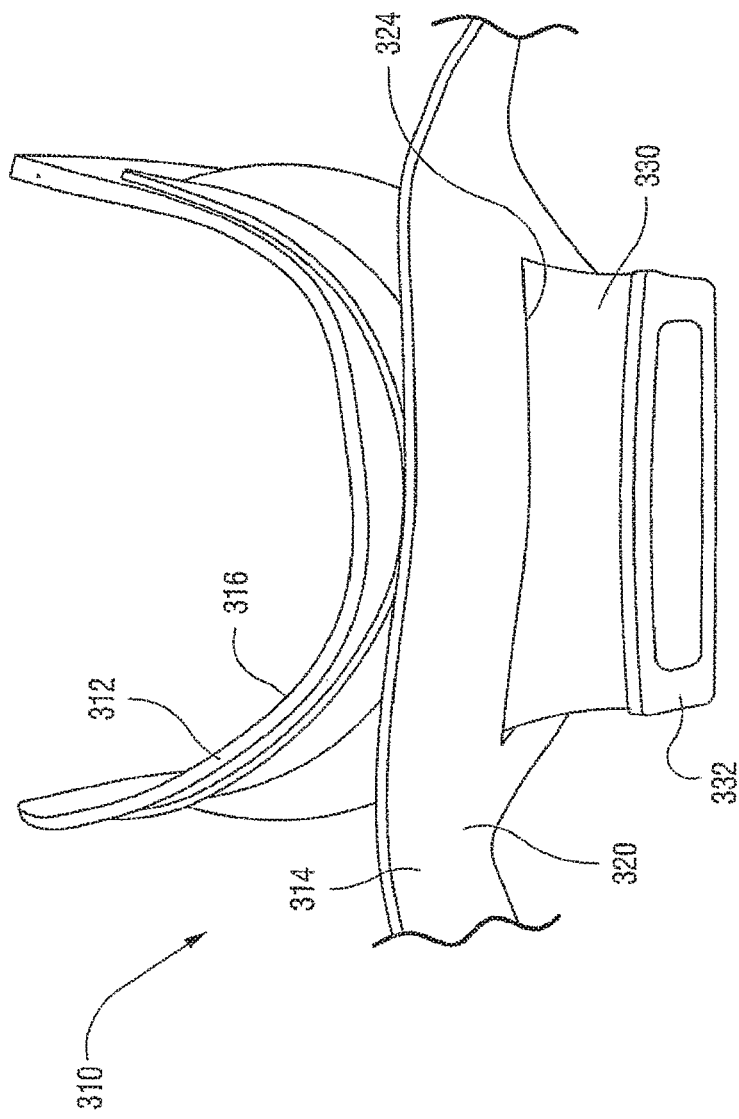
FIG. 9 is a top view of the mouth seal assembly shown in FIG. 7 isolated from the nasal mask system.

FIGS. 7-10 illustrate a mouth seal assembly 310 according to another embodiment of the present invention. As illustrated in FIGS. 7-8, the mouth seal assembly 310 is used in conjunction with a nasal mask 350 adapted to form a seal with the patient's nose. The nasal mask 350 includes a nasal cushion/frame assembly 360 structured to seal around the patient's nose in use, and headgear 370 attached to the nasal cushion/frame assembly 360 to maintain the nasal cushion/frame assembly 360 in a desired position on the patient's face.

The illustrated nasal mask 350 is commercially sold under the name of MIRAGE® by ResMed Ltd. Further details and embodiments of this nasal mask 350 are disclosed in U.S. Pat. No. 6,112,746, the entirety being incorporated herein by reference. While the mouth seal assembly 310 is described as being used in conjunction with a nasal mask of the type described above, it may be implemented into other nasal masks. That is, the nasal mask 350 is merely exemplary, and the mouth seal assembly 310 may be used in conjunction with any suitable nasal mask, e.g., nasal assembly, nasal prongs, nasal pillows, nasal cannulae, nasal inserts, nozzles, etc.

The mouth seal assembly 310 includes a mouth seal 312 adapted to form a seal with the patient's mouth and a strap arrangement 314 attached to the mouth seal 312 to maintain the mouth seal 312 in a desired position on the patient's face. In the illustrated embodiment, the mouth seal 312 includes a curved strip of silicone 316 or similar flexible material that generally conforms to the curvature of the patient's mouth region (see FIGS. 9 and 10). The mouth seal 312 includes a length and height sufficient to completely cover the patient's mouth.

Figure 10:
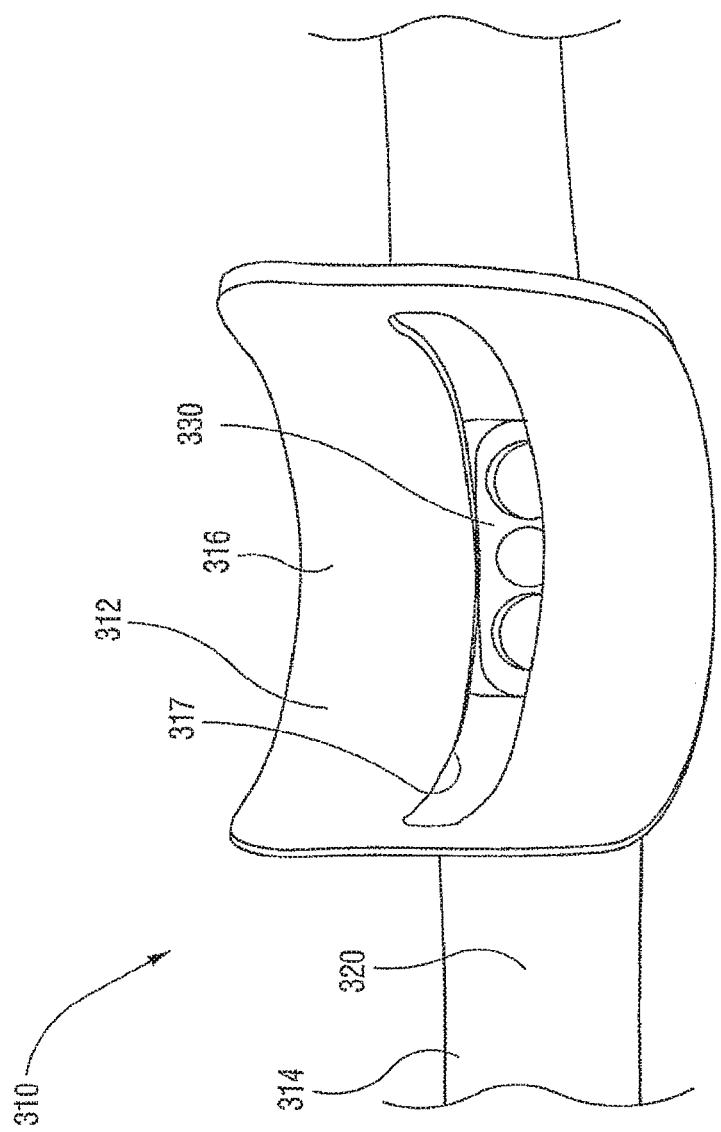
FIG. 10 is a rear view of the mouth seal assembly shown in FIG. 7 isolated from the nasal mask system.

The mouth seal assembly 310 also includes an anti-asphyxia valve 330 that provides an air passage to the patient in the absence of pressure. The anti-asphyxia valve 330 is provided to the mouth seal 312 over the patient's lips to allow the patient to breathe in freely in the absence of pressure but prevent exhalation in the presence of air pressure. As shown in FIG. 10, a slit 317 is provided in the silicone 316 to communicate the anti-asphyxia valve 330 with the patient's mouth.

In an alternative embodiment, the mouth seal assembly 310 may be used without the anti-asphyxia valve 330. In this embodiment, the patient may open his/her mouth to breath when air pressure is not present, e.g., in the case of a power supply failure. This is possible since a seal is formed by air pressure causing the patient's lips to "bellow". Thus, the seal is only "activated" when air pressure is present.

The mouth seal 312 is held against the patient's lips by the strap arrangement 314 which includes a strap 320 that extends along the sides of the patient's face. At least one end of the strap 320 includes a VELCRO® section 322 that allows the end to adjustably attach to a respective lower strap 372 of the nasal mask headgear 370 (see FIG. 8).

However, the strap arrangement 314 may be independent of the nasal mask headgear 370, e.g., extend around the back of the patient's neck.

In the illustrated embodiment, the strap 320 of the headgear arrangement 314 includes an opening 324 adapted to receive the anti-asphyxia valve 330 therethrough. The anti-asphyxia valve 330 protrudes from the mouth seal 312 and includes a flange 332 that retains the strap 320 to the anti-asphyxia valve 330 and hence the mouth seal 312. However, the mouth seal 312 may be attached to the headgear arrangement 314 in any other suitable manner.

Similar to the mouth seal assembly 10 described above, the mouth seal assembly 310 is independent from the supply of pressurized air and the patient's lips conform to the mouth seal 312 due to the differential pressure between the patient's mouth and the outside of the mouth seal.

4. Fourth Embodiment of Mouth Seal Assembly

Figure 11:
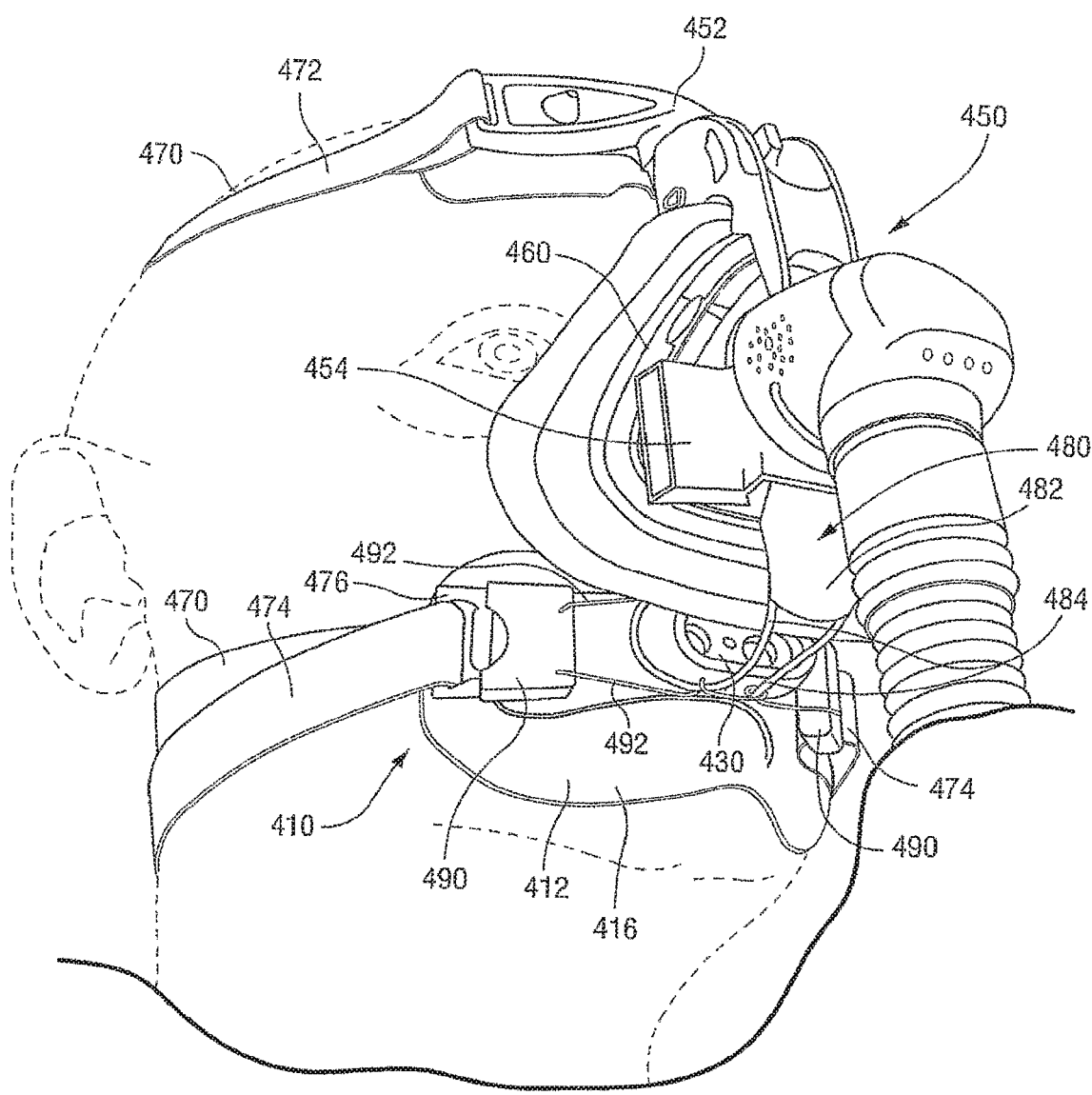
FIG. 11 is a perspective view of a mouth seal assembly according to another embodiment of the present invention, the mouth seal assembly being used in conjunction with a nasal mask system.

FIG. 11 illustrates a mouth seal assembly 410 according to another embodiment of the present invention. As illustrated, the mouth seal assembly 410 is used in conjunction with a nasal mask 450 adapted to form a seal with the patient's face. The nasal mask 450 includes a nasal cushion/frame assembly 460 structured to seal around the patient's nose in use, and headgear 470 attached to the nasal cushion/frame assembly 460 to maintain the nasal cushion/frame assembly 460 in a desired position on the patient's face.

The illustrated nasal mask 450 is commercially sold under the name of ACTIVA® by ResMed Ltd. Further details and embodiments of this nasal mask 450 are disclosed in U.S. patent application Ser. No. 10/655,622, filed Sep. 5, 2003, now U.S. Pat. No. 7,523,754, the entirety being incorporated herein by reference. While the mouth seal assembly 410 is described as being used in conjunction with a nasal mask of the type described above, it may be implemented into other nasal masks. That is, the nasal mask 450 is merely exemplary, and the mouth seal assembly 410 may be used in conjunction with any suitable nasal mask, e.g., nasal assembly, nasal prongs, nasal pillows, nasal cannulae, nasal inserts, nozzles, etc.

The mouth seal assembly 410 includes a mouth seal 412 adapted to form a seal with the patient's mouth. In the illustrated embodiment, the mouth seal 412 includes a strip of silicone 416 or similar flexible material that generally conforms to the curvature of the patient's mouth region. The mouth seal 412 includes a length and height sufficient to completely cover the patient's mouth.

The mouth seal assembly 410 also includes an anti-asphyxia valve 430 that provides an air passage to the patient in the absence of pressure. The anti-asphyxia valve 430 is provided to the mouth seal 412 over the patient's lips to allow the patient to breathe in freely in the absence of pressure but prevent exhalation in the presence of pressure.

In an alternative embodiment, the mouth seal assembly 410 may be used without the anti-asphyxia valve 430. In this embodiment, the patient may open his/her mouth to breath when air pressure is not present, e.g., in the case of a power supply failure. This is possible since a seal is formed by air pressure causing the patient's lips to "bellow". Thus, the seal is only "activated" when air pressure is present.

In the illustrated embodiment, the mouth seal assembly 410 is attached to the nasal mask 450. In addition, the headgear 470 of the nasal mask 450 is attached to the mouth seal assembly 410 to hold the mouth seal 412 against the patient's lips as well as hold a lower portion of the nasal cushion/frame assembly 460 against the patient's nasal region.

Specifically, a support structure 480 is provided to attach the mouth seal assembly 410 to the nasal mask 450. In the illustrated embodiment, the support structure 480 includes an anchor 482 attached to the nasal cushion/frame assembly 460 and a wire arrangement 484 that wraps around the anti-asphyxia valve 430 to connect the mouth seal assembly 410 to the anchor 482. However, the mouth seal assembly 410 may be attached to the nasal mask 450 in other suitable manners.

The headgear 470 of the nasal mask 450 includes upper straps 472 attached to a forehead support 452 of the nasal mask 450 and lower straps 474 that are removably attached to the mouth seal assembly 410. As illustrated, the end of each lower strap 474 includes a clip 476 that is adapted to engage a respective clip receiver 490 provided to the mouth seal assembly 410. The clip receivers 490 are attached to the mouth seal assembly by a wire arrangement 492 that wraps around the wire arrangement 484 associated with the nasal mask 450. However, the clip receivers 490 may be attached to the mask seal assembly 410 in other suitable manners. In addition, the lower straps 474 may be attached to the mask seal assembly 410 in other suitable manners.

In use, the upper and lower straps 472, 474 maintain the nasal mask 450 and the mouth seal 412 in a desired position on the patient's face. In another embodiment, the mouth seal assembly 410 may be independent from the nasal mask 450 and a separate strap arrangement may be provided to secure the mouth seal assembly 410 to the patient's head. In this arrangement, clips may be provided to the lower straps 474 that are adapted to engage respective clip receivers 454 provided to the nasal cushion/frame assembly 460.

Similar to the mouth seal assembly 10 described above, the mouth seal assembly 410 is independent from the supply of pressurized air and the patient's lips conform to the mouth seal 412 due to the differential pressure between the patient's mouth and the outside of the mouth seal.

5. Fifth Embodiment of Mouth Seal Assembly

Figure 12:
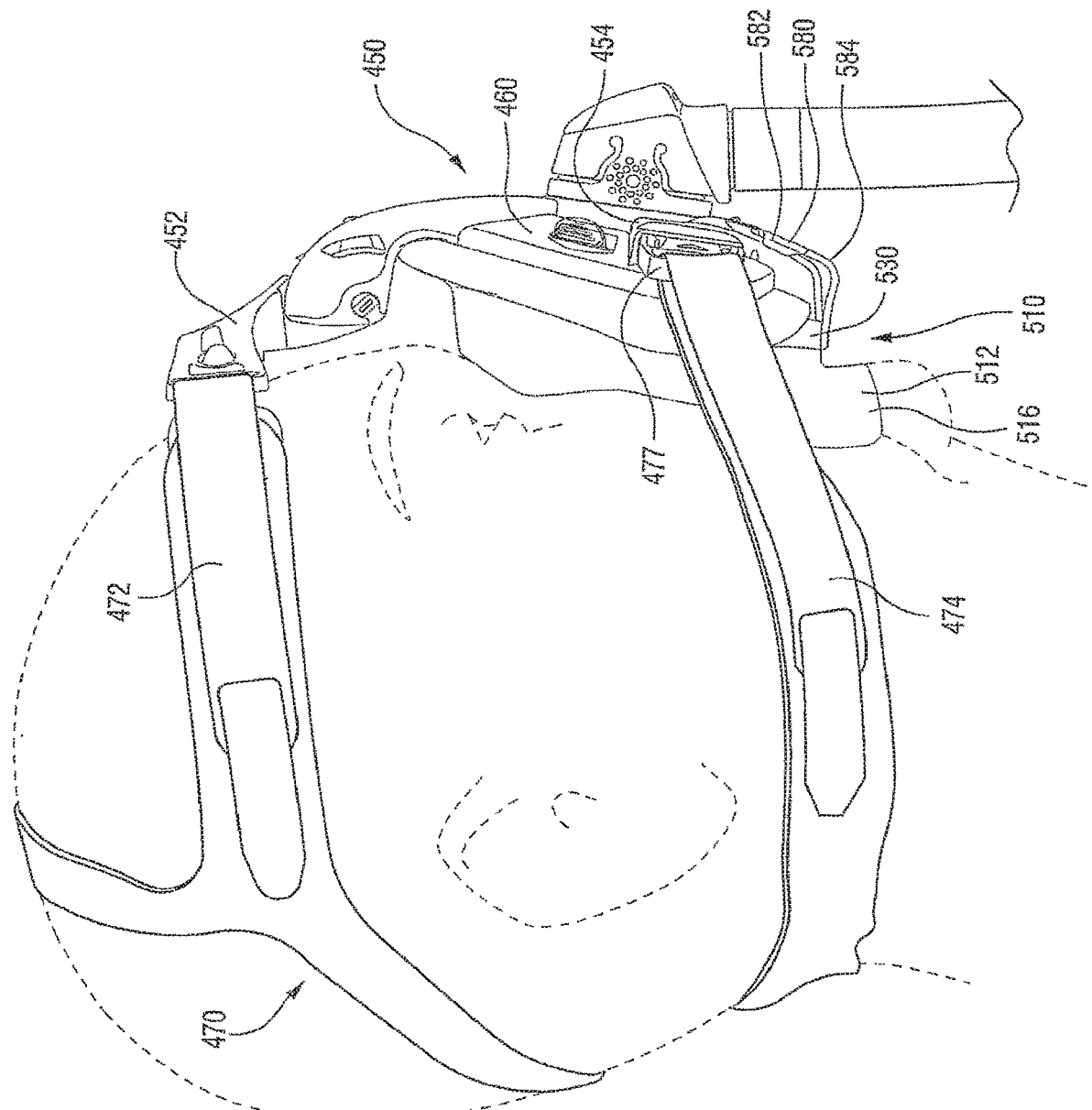
FIG. 12 is a side view of a mouth seal assembly according to yet another embodiment of the present invention, the mouth seal assembly being used in conjunction with a nasal mask system.
Figure 13:
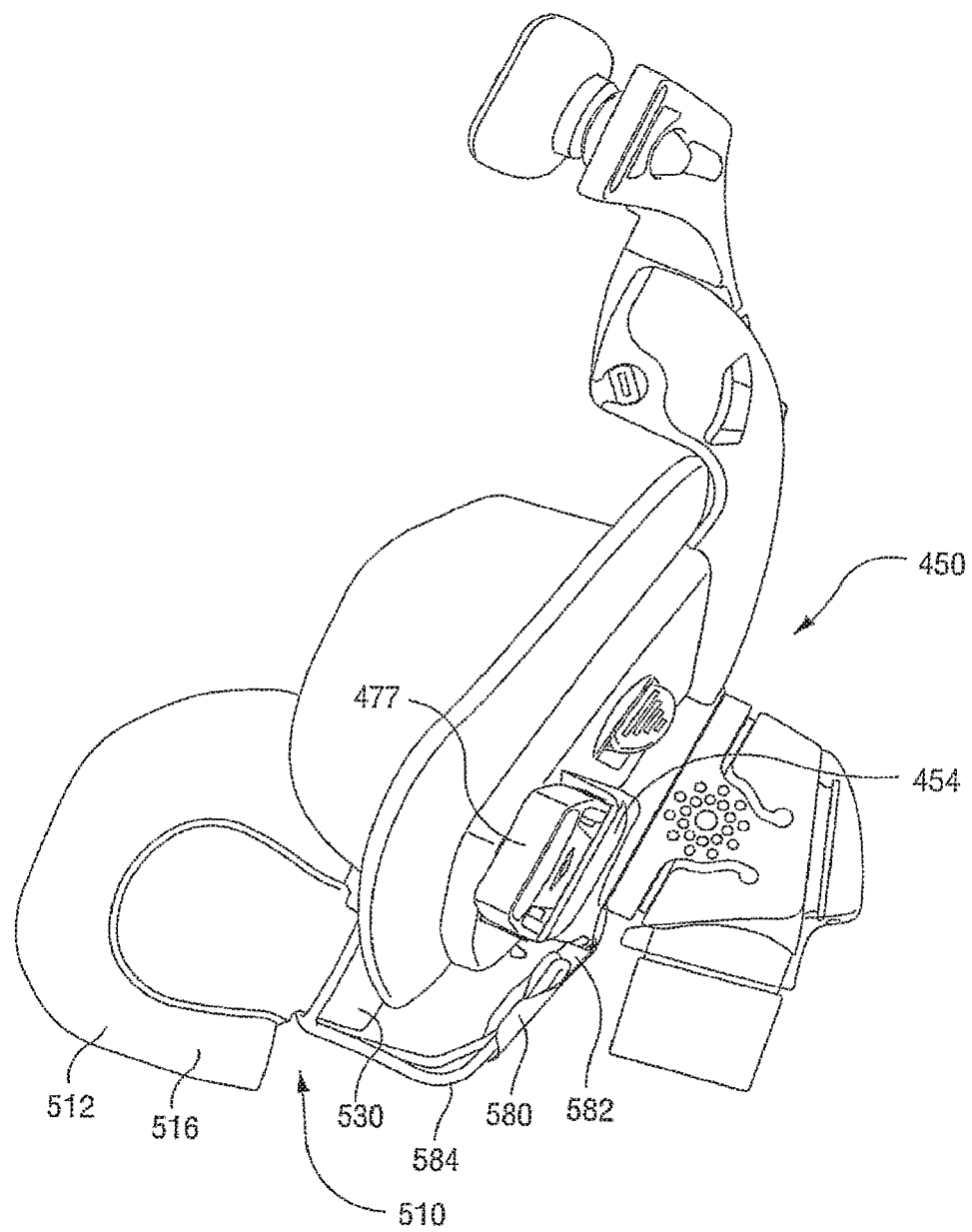
FIG. 13 is a side view of the mouth seal assembly and nasal mask system shown in FIG. 12 removed from the patient's head.
Figure 14:
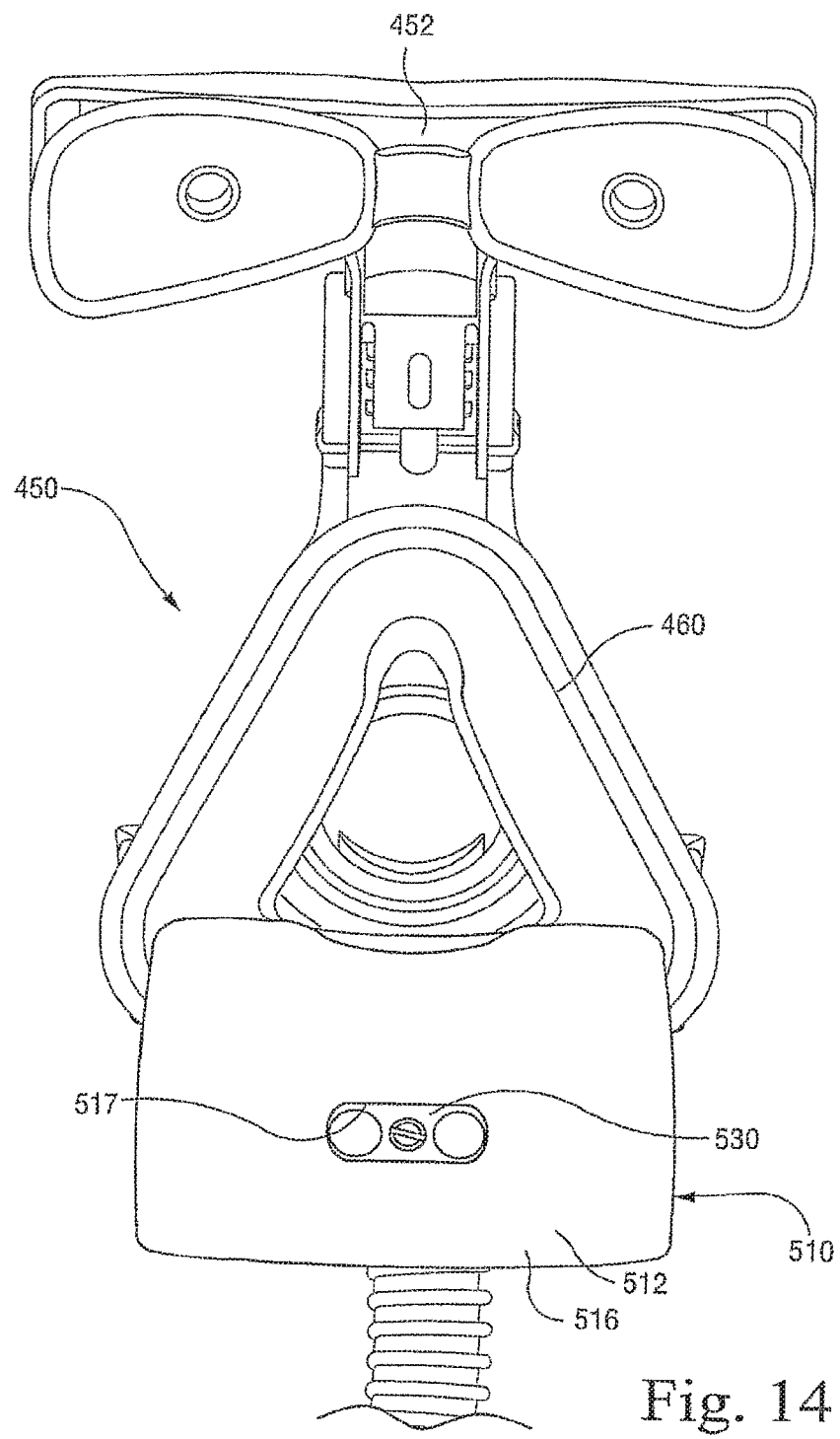
FIG. 14 is a rear view of the mouth seal assembly and nasal mask system shown in FIG. 12 removed from the patient's head.

FIGS. 12-14 illustrate a mouth seal assembly 510 according to another embodiment of the present invention. As illustrated, the mouth seal assembly 510 is used in conjunction with an ACTIVA® nasal mask 450. The ACTIVA® nasal mask 450 is indicated with similar reference numerals as described above. While the mouth seal assembly 510 is described as being used in conjunction with a nasal mask of the type described above, it may be implemented into other nasal masks. That is, the nasal mask 450 is merely exemplary, and the mouth seal assembly 510 may be used in conjunction with any suitable nasal mask, e.g., nasal assembly, nasal prongs, nasal pillows, nasal cannulae, nasal inserts, nozzles, etc.

The mouth seal assembly 510 includes a mouth seal 512 adapted to form a seal with the patient's mouth. In the illustrated embodiment, the mouth seal 512 includes a curved strip of silicone 516 or similar flexible material that generally conforms to the curvature of the patient's mouth region. The mouth seal 512 includes a length and height sufficient to completely cover the patient's mouth.

The mouth seal assembly 510 also includes an anti-asphyxia valve 530 that provides an air passage to the patient in the absence of pressure. The anti-asphyxia valve 530 is provided to the mouth seal 512 over the patient's lips to allow the patient to breathe in freely in the absence of pressure but prevent exhalation in the presence of pressure. As shown in FIG. 14, a slit 517 is provided in the silicone 516 to communicate the anti-asphyxia valve 530 with the patient's mouth.

In an alternative embodiment, the mouth seal assembly 510 may be used without the anti-asphyxia valve 530. In this embodiment, the patient may open his/her mouth to breath when air pressure is not present, e.g., in the case of a power supply failure. This is possible since a seal is formed by air pressure causing the patient's lips to "bellow". Thus, the seal is only "activated" when air pressure is present.

In the illustrated embodiment, the mouth seal assembly 510 is attached to the nasal mask 450. In addition, the headgear 470 of the nasal mask 450 is adapted to hold the mouth seal 512 against the patient's lips as well as hold a lower portion of the nasal cushion/frame assembly 460 against the patient's nasal region.

Specifically, a support structure 580 is provided to attach the mouth seal assembly 510 to the nasal mask 450. In the illustrated embodiment, the support structure 580 includes an anchor 582 attached to the nasal cushion/frame assembly 460 and a wire arrangement 584 that wraps around the anti-asphyxia valve 530 to connect the mouth seal assembly 510 to the anchor 582. However, the mouth seal assembly 510 may be attached to the nasal mask 450 in other suitable manners.

The headgear 470 of the nasal mask 450 includes upper straps 472 attached to a forehead support 452 of the nasal mask 450 and lower straps 474 attached to a lower portion of the nasal cushion/frame assembly 460. Specifically, the end of each lower strap 474 includes a clip 477 that is adapted to be engaged within a respective clip receiver 454 provided to the nasal cushion/frame assembly 460. In use, the upper and lower straps 472, 474 maintain the nasal mask 450 and the mouth seal 512 in a desired position on the patient's face. In another embodiment, the mouth seal assembly 510 may be independent from the nasal mask 450 and a separate strap arrangement may be provided to secure the mouth seal assembly 510 to the patient's head.

Similar to the mouth seal assembly 10 described above, the mouth seal assembly 510 is independent from the supply of pressurized air and the patient's lips conform to the mouth seal 512 due to the differential pressure between the patient's mouth and the outside of the mouth seal.

6. Sixth Embodiment of Mouth Seal Assembly

Figure 15:
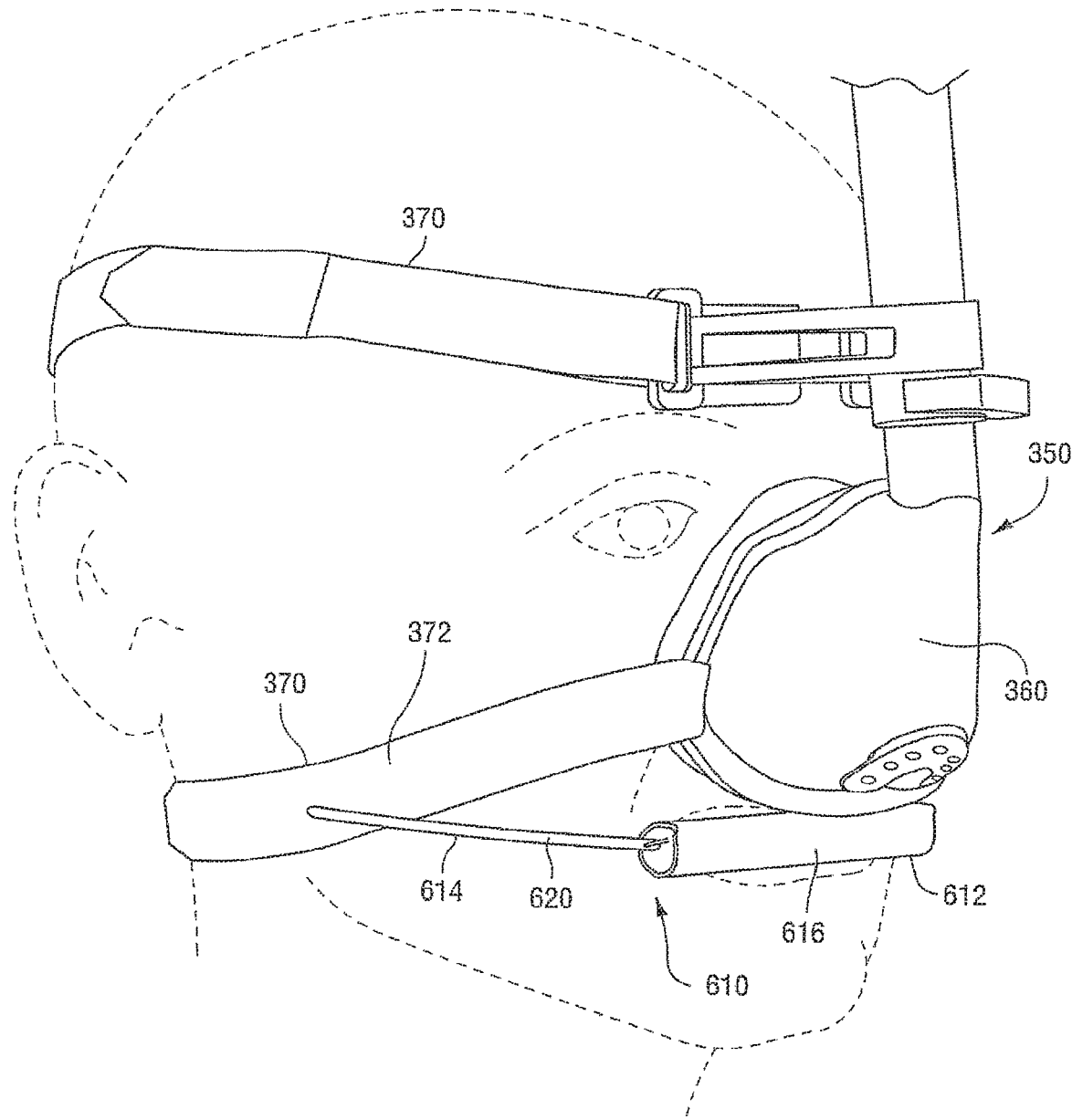
FIG. 15 is a perspective view of a mouth seal assembly according to still another embodiment of the present invention, the mouth seal assembly being used in conjunction with a nasal mask system.
Figure 16:
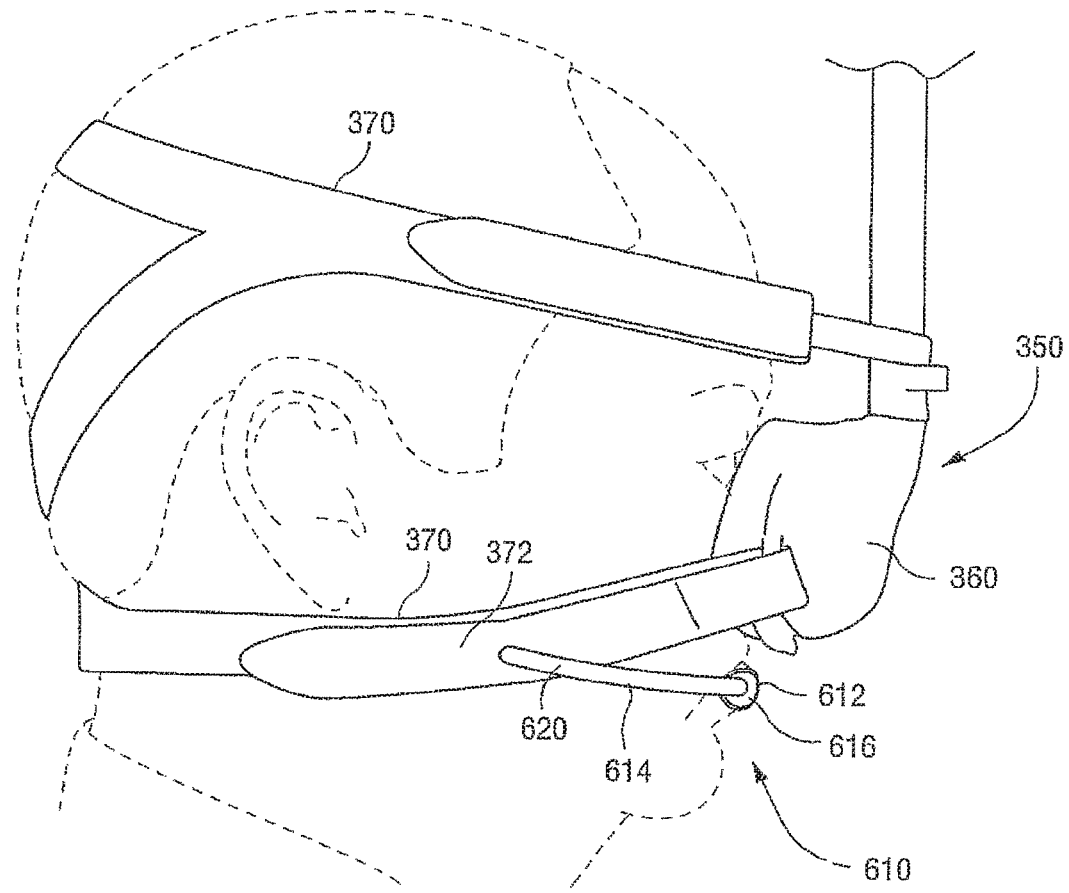
FIG. 16 is a side view of the mouth seal assembly and nasal mask system shown in FIG. 15.
Figure 18:
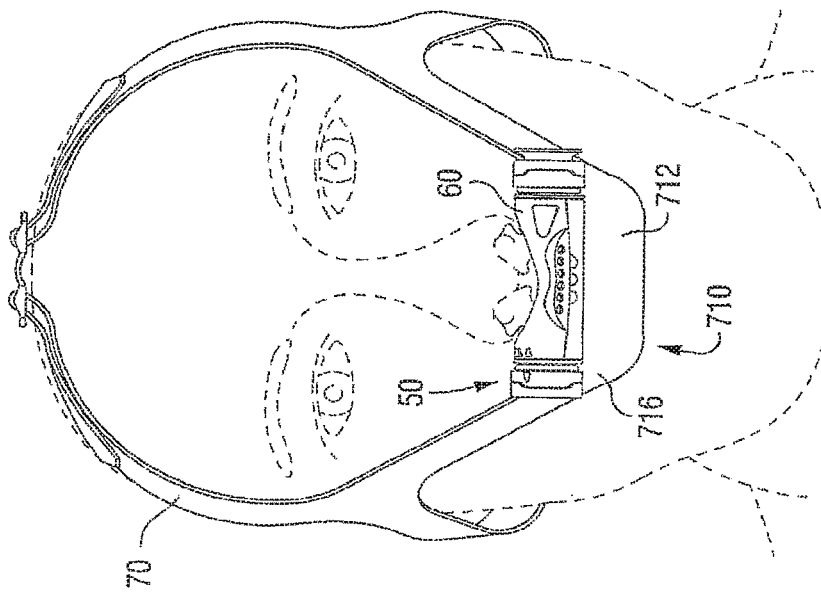
FIGS. 17-20 are various views of a mouth seal assembly according to another embodiment of the present invention, the mouth seal assembly being used in conjunction with a nasal mask system.
Figure 17:
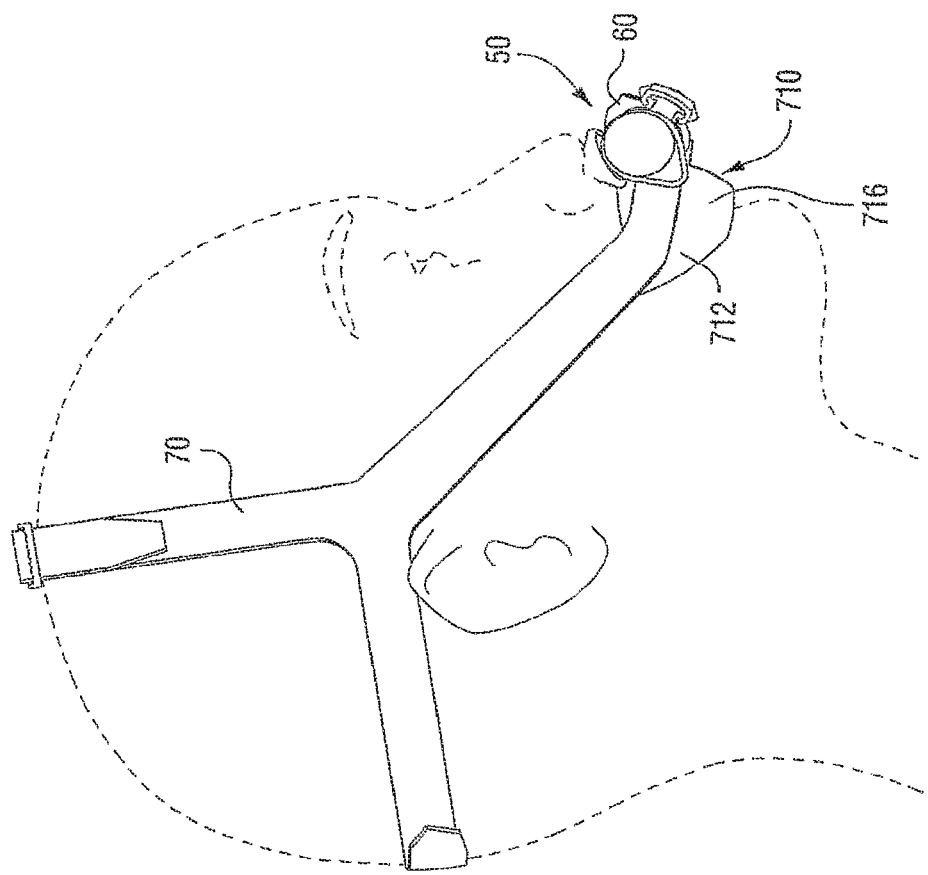

FIGS. 15 and 16 illustrate a mouth seal assembly 610 according to another embodiment of the present invention. As illustrated, the mouth seal assembly 610 is used in conjunction with an MIRAGE® nasal mask 350. The MIRAGE® nasal mask 350 is indicated with similar reference numerals as described above. While the mouth seal assembly 610 is described as being used in conjunction with a nasal mask of the type described above, it may be implemented into other nasal masks. That is, the nasal mask 350 is merely exemplary, and the mouth seal assembly 610 may be used in conjunction with any suitable nasal mask, e.g., nasal assembly, nasal prongs, nasal pillows, nasal cannulae, nasal inserts, nozzles, etc.

The mouth seal assembly 610 includes a mouth seal 612 adapted to form a seal with the patient's mouth and a strap arrangement 614 attached to the mouth seal 612 to maintain the mouth seal 612 in a desired position on the patient's face. In the illustrated embodiment, the mouth seal 612 includes an elongated substantially rigid tube 616 that sits on the patient's lips. The tube 616 may have a solid or hollow configuration, and includes a length sufficient to extend along the patient's lips.

The tube 616 is held against the patient's lips by the strap arrangement 614 which includes side straps 620 that extend along the sides of the patient's face. One end of each strap 620 is attached to a respective end of the tube 616, e.g., by hook mechanism, and the opposing end of each strap 620 is attached to a respective lower strap 372 of the nasal mask headgear 370, e.g., by a clip mechanism, hook and loop fasteners, etc. However, the strap arrangement 614 may be independent of the nasal mask headgear 370, e.g., extend around the back of the patient's neck.

The tube 616 is independent from the supply of pressurized air. The tube 616 provides a surface upon which the patient's lips are pushed due to mouth leak and thus form a seal. This mechanism provides a seal that is "activated" when pressure is applied to the mask, however in the event of power failure or lack or pressure, the seal is not "activated" and thus the patient can open his/her mouth to breath.

7. Seventh Embodiment of Mouth Seal Assembly

FIGS. 17 to 20 illustrate a mouth seal assembly 710 according to another embodiment of the present invention. As illustrated, the mouth seal assembly 710 is used in conjunction with a SWIFT® nasal mask 50. The SWIFT® nasal mask 50 is indicated with similar reference numerals as described above. While the mouth seal assembly 710 is described as being used in conjunction with a nasal mask of the type described above, it may be implemented into other nasal masks. That is, the nasal mask 50 is merely exemplary, and the mouth seal assembly 710 may be used in conjunction with any suitable nasal mask.

Figure 20:
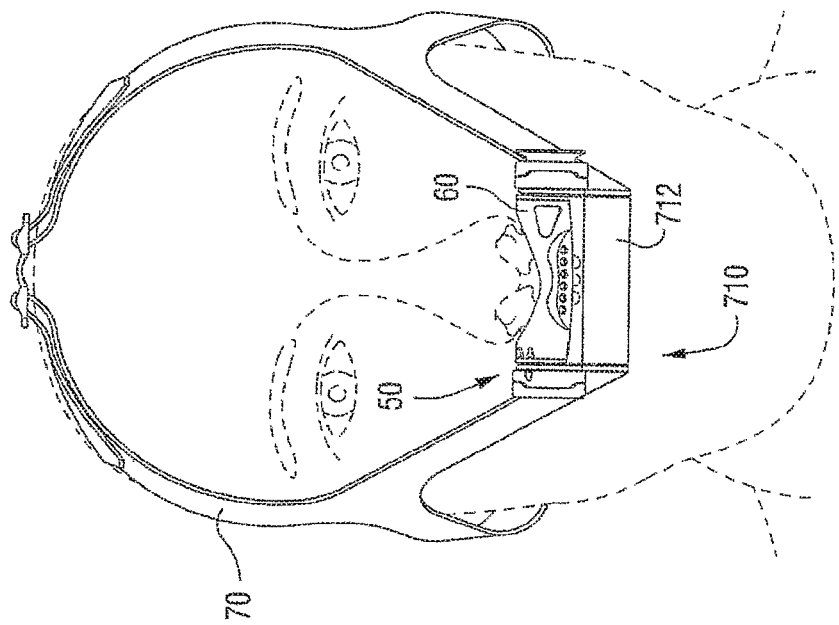
Figure 19:
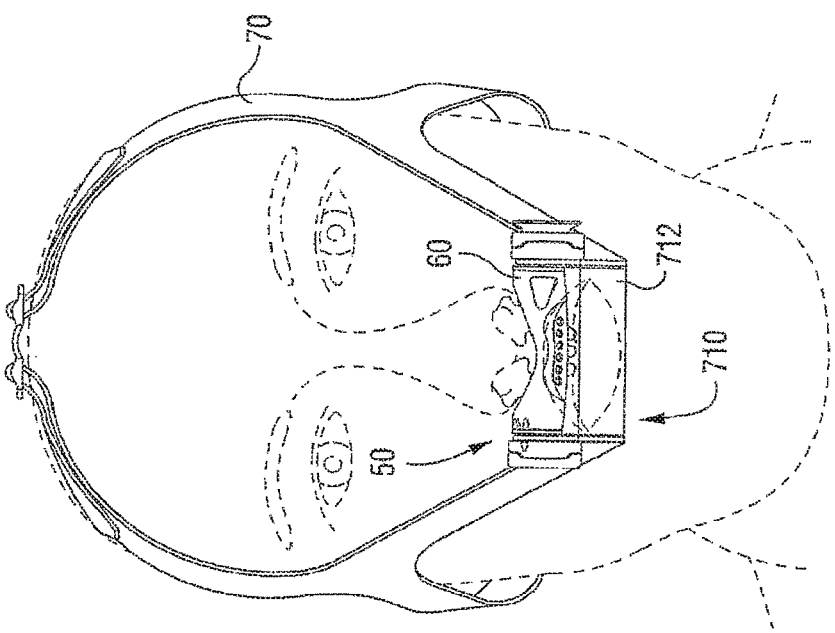

The mouth seal assembly 710 includes a mouth seal 712 adapted to form a seal with the patient's mouth. In the illustrated embodiment, the mouth seal 712 includes a curved strip of silicone 716 or similar flexible material that generally conforms to the curvature of the patient's mouth region (e.g., see FIG. 17). The mouth seal 712 includes a length and height sufficient to completely cover the patient's mouth. FIGS. 19 and 20 illustrate transparent and solid views of the mouth seal 712 to show the mouth seal 712 in relation to the patient's mouth.

In the illustrated embodiment, the mouth seal 712 is maintained in a desired position by the headgear 70 and/or the nasal assembly 60 of the nasal mask 50. The headgear 70 and/or nasal assembly 60 may be modified to support the mouth seal 712 in place. Thus, the mouth seal 712 is maintained in position without its own strap arrangement. However, the mouth seal 712 may be supported in other suitable manners.

Similar to the mouth seal assembly 10 described above, the mouth seal assembly 710 is independent from the supply of pressurized air and the patient's lips conform to the mouth seal 712 due to the differential pressure between the patient's mouth and the outside of the mouth seal. The mouth seal 712 may be provided with or without an anti-asphyxia valve.

8. Eighth Embodiment of Mouth Seal Assembly

Figure 21:
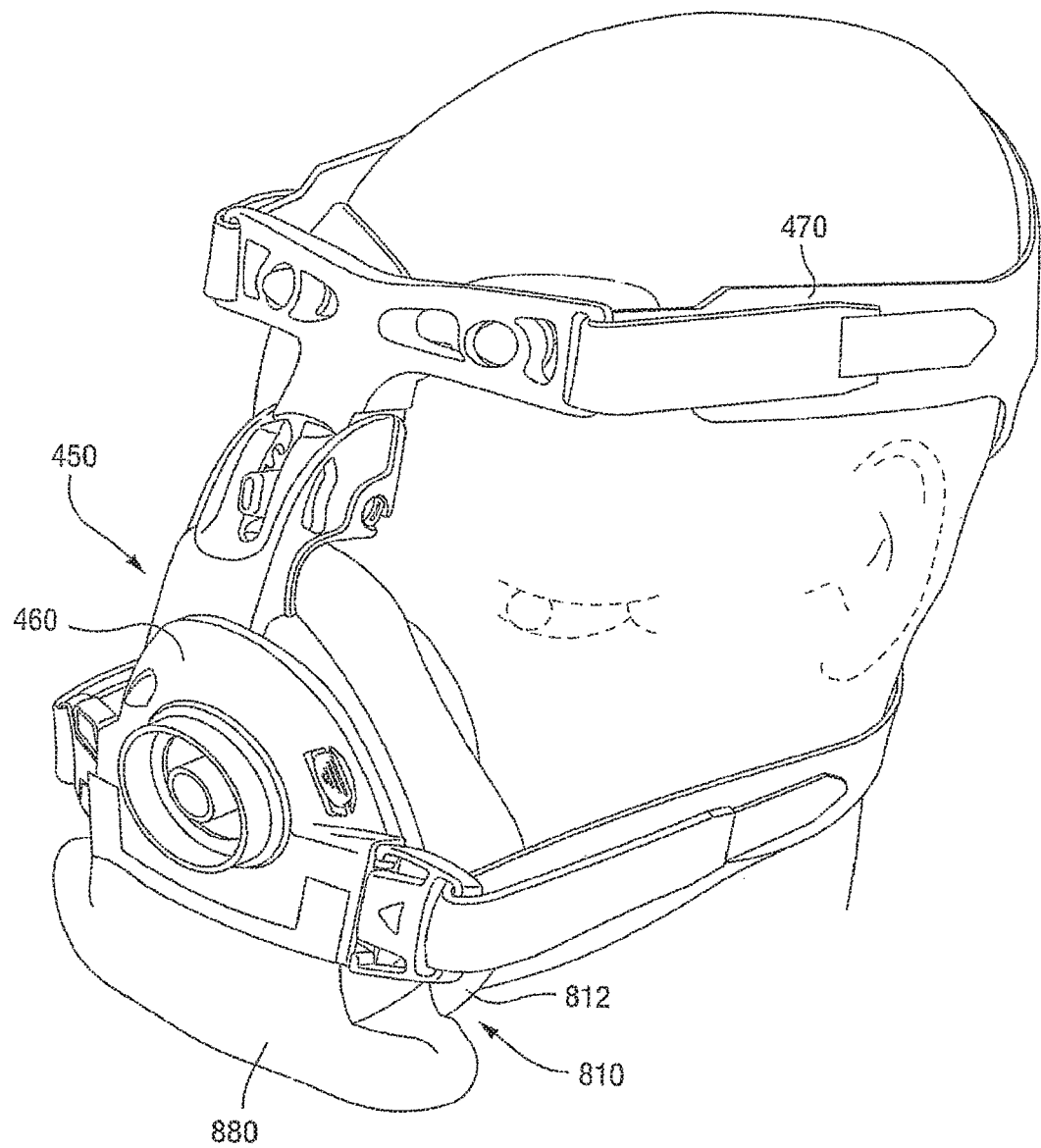
FIGS. 21-23 are various views of a mouth seal assembly according to another embodiment of the present invention, the mouth seal assembly being used in conjunction with a nasal mask system.
Figure 22:
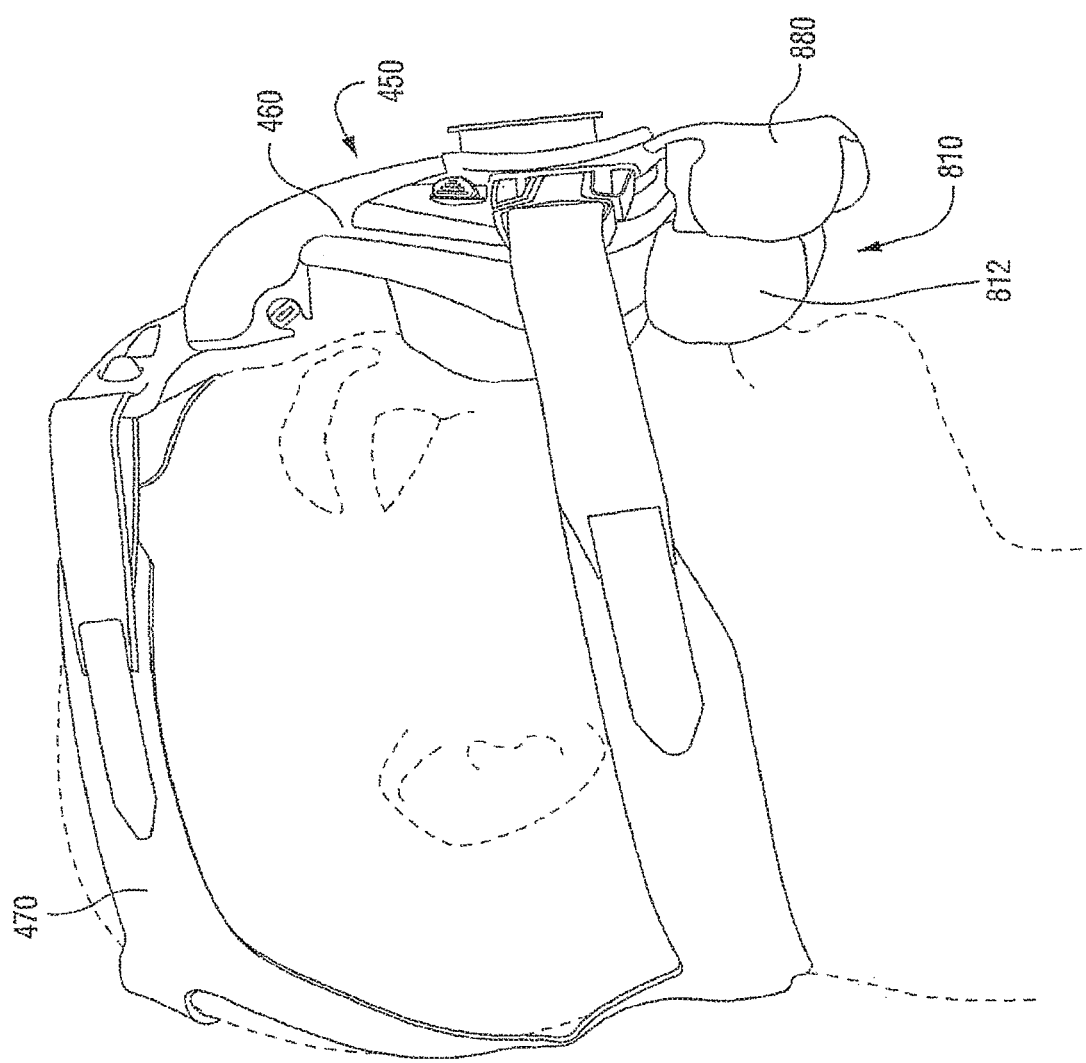
Figure 23:
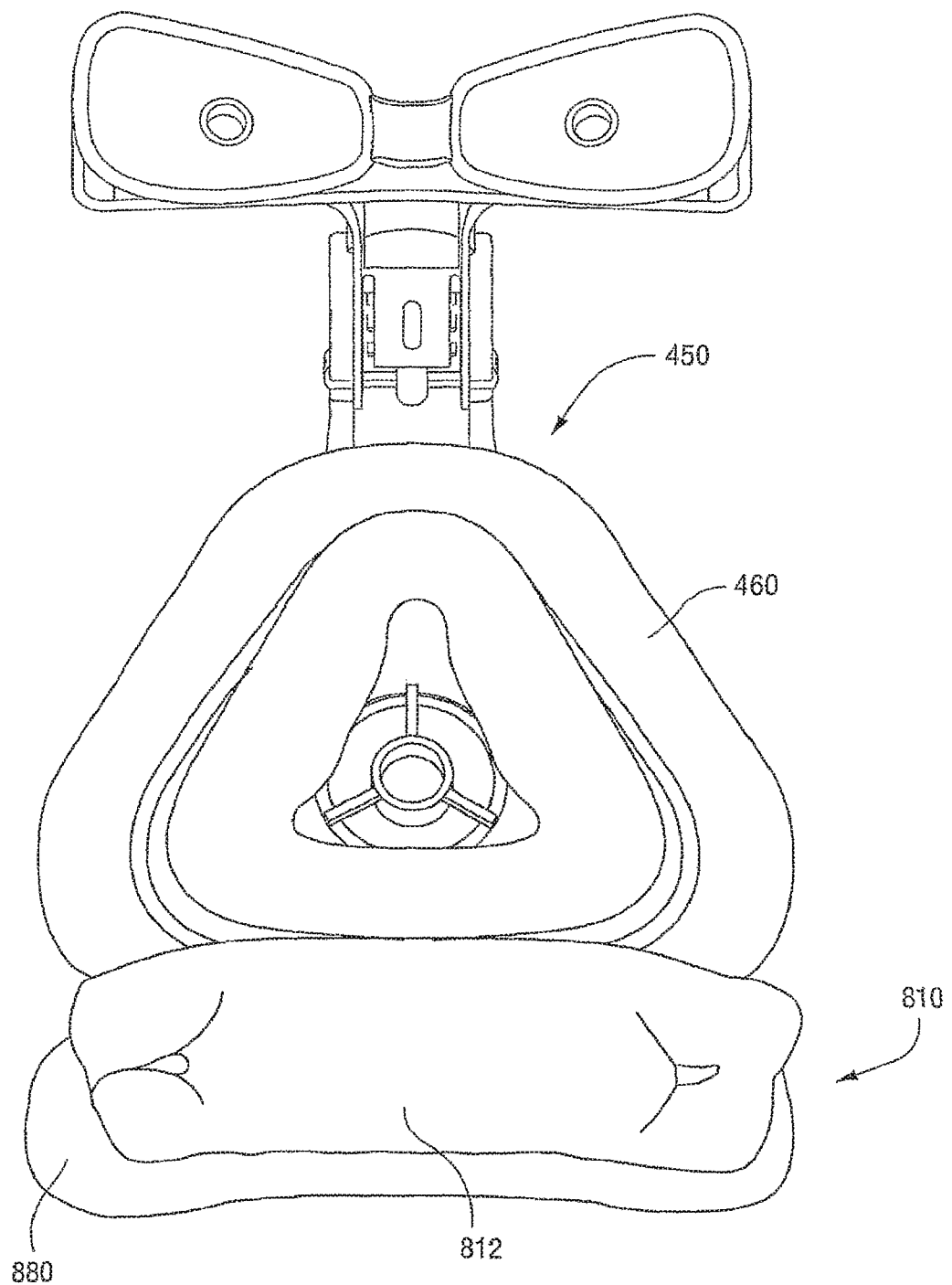

FIGS. 21 to 23 illustrate a mouth seal assembly 810 according to another embodiment of the present invention. As illustrated, the mouth seal assembly 810 is used in conjunction with an ACTIVA® nasal mask 450. The ACTIVA® nasal mask 450 is indicated with similar reference numerals as described above. While the mouth seal assembly 810 is described as being used in conjunction with a nasal mask of the type described above, it may be implemented into other nasal masks. That is, the nasal mask 450 is merely exemplary, and the mouth seal assembly 810 may be used in conjunction with any suitable nasal mask, e.g., nasal assembly, nasal prongs, nasal pillows, nasal cannulae, nasal inserts, nozzles, etc.

The mouth seal assembly 810 includes a mouth seal 812 adapted to form a seal with the patient's mouth and a support structure or mount 880 to support the mouth seal 812 on the nasal mask 450. In the illustrated embodiment, the mouth seal 812 is formed with foam, e.g., foam-filled cylinder or strip, and provides a foam seal or interface with the patient's mouth. The foam mouth seal 812 includes a length and height sufficient to completely cover the patient's mouth. In an alternative embodiment, the foam mouth seal 812 may be shaped to better fit the facial profile around the patient's lips, e.g., see FIG. 25 described below.

The foam mouth seal 812 provides a compliant seal that comfortably engages the patient's mouth. The compliant nature of the foam ensures that it deforms to seal against a range of facial profiles. That is, the foam can deform to the appropriate size and shape without compromising the seal and without adding discomfort to the patient.

When the nasal mask 450 is pressurized, the patients lips will "bellow" to engage the foam mouth seal 812 and form a seal that substantially prevents mouth leak and mouth breathing. If the nasal mask 450 is not pressurized, e.g., in the case of a power supply failure, the foam mouth seal 812 is not "activated" and the patient is free to open his/her mouth to breathe. In an alternative embodiment, an anti-asphyxia valve may be provided to the mouth seal or the air supply to the mask. Also, the mouth seal 812 may alternatively be filled with gel, silicone, or air to provide a similar compliant seal.

The support structure or mount 880 is preferably lightweight and may be constructed of a polycarbonate or steel material, for example. The support structure 880 may be mounted to the nasal mask and mouth seal 812 in any suitable manner. In an embodiment, the support structure 880 may be biased, e.g., spring biased, to provide the mouth seal 812 with a sealing force onto the patient's mouth. However, the mouth seal 812 may be attached to the nasal mask 450 in other suitable manners. For example, existing structures on the nasal mask may be used to support the mouth seal. In an embodiment, the mount may be supported by one or more ports typically provided on nasal masks (and typically closed by a ports cap). In another embodiment, the mount may be supported by headgear clips associated with the nasal mask headgear. The headgear clip may be modified to incorporate the mount.

Similar to the mouth seal assembly 10 described above, the mouth seal assembly 810 is independent from the supply of pressurized air and the patient's lips conform to the mouth seal 812 due to the differential pressure between the patient's mouth and the outside of the mouth seal.

9. Ninth Embodiment of Mouth Seal Assembly

Figure 24:
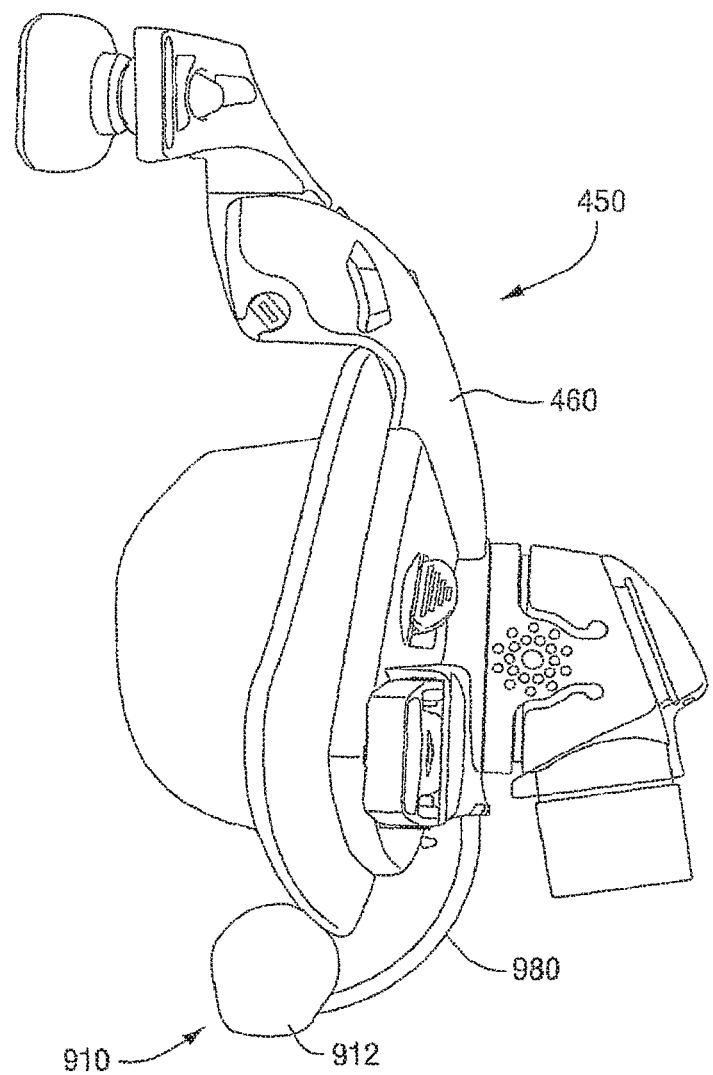
FIG. 24 is a side view of a mouth seal assembly according to another embodiment of the present invention, the mouth seal assembly being used in conjunction with a nasal mask system.

FIG. 24 illustrates a mouth seal assembly 910 according to another embodiment of the present invention. As illustrated, the mouth seal assembly 910 is used in conjunction with an ACTIVA® nasal mask 450. The ACTIVA® nasal mask 450 is indicated with similar reference numerals as described above. While the mouth seal assembly 910 is described as being used in conjunction with a nasal mask of the type described above, it may be implemented into other nasal masks. That is, the nasal mask 450 is merely exemplary, and the mouth seal assembly 910 may be used in conjunction with any suitable nasal mask, e.g., nasal assembly, nasal prongs, nasal pillows, nasal cannulae, nasal inserts, nozzles, etc.

The mouth seal assembly 910 includes a mouth seal 912 adapted to form a seal with the patient's mouth and a support structure or mount 980 to support the mouth seal 912 on the nasal mask 450. In the illustrated embodiment, the mouth seal 912 is formed with foam, e.g., foam-filled cylinder or strip, and provides a foam seal or interface with the patient's mouth. Similar to mouth seal 812 described above, the foam mouth seal 912 provides a compliant seal that comfortably engages the patient's mouth. In alternative embodiments, the mouth seal 912 may be filled with gel, silicone, or air to provide a similar compliant seal.

Figure 25:
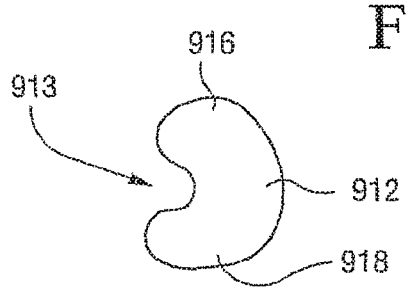
FIG. 25 is a side view of a mouth seal according to another embodiment of the present invention.

As shown in FIG. 25, the foam mouth seal 912 may be shaped to better fit the facial profile around the patient's lips. In use, the patient's lips would fit within the space 913 provided between upper and lower protrusions 916, 918 of the foam mouth seal 912.

The support structure or mount 980 is preferably lightweight and may be constructed of a polycarbonate or steel material, for example. The support structure 980 may be mounted to the nasal mask and mouth seal 912 in any suitable manner. In an embodiment, the support structure 980 may be biased, e.g., constructed of spring steel with a spring bias, to provide the mouth seal 912 with a sealing force onto the patient's mouth. However, the mouth seal 912 may be attached to the nasal mask 450 in other suitable manners.

Similar to the mouth seal assembly 10 described above, the mouth seal assembly 910 is independent from the supply of pressurized air and the patient's lips conform to the mouth seal 912 due to the differential pressure between the patient's mouth and the outside of the mouth seal. The mouth seal 912 may be provided with or without an anti-asphyxia valve.

10. Alternative Embodiments of Mouth Seal

FIGS. 26-30 illustrate mouth seals according to alternative embodiments of the present invention. Each mouth seal may be used in conjunction with a nasal mask such as the SWIFT®, MIRAGE®, and ACTIVA® nasal masks 50, 350, 450 described above.

Figure 26:
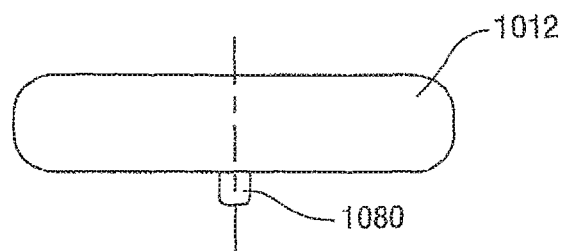
FIGS. 26-30 are top views of mouth seals according to alternative embodiments of the present invention.

FIG. 26 illustrates a mouth seal 1012 formed with foam, e.g., foam-filled cylinder or strip, that provides a foam seal or interface with the patient's mouth. A mount 1080 is provided to the mouth seal 1012 to support the mouth seal 1012 on a nasal mask. The foam mouth seal 1012 is similar to the foam mouth seals 812, 912 described above.

Figure 27:
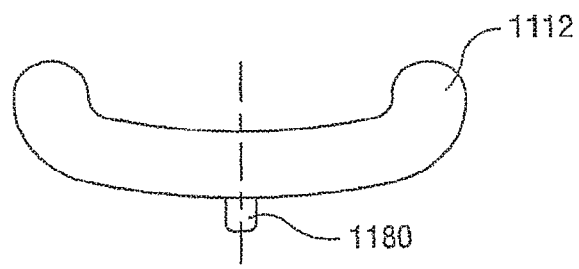

FIG. 27 illustrates a mouth seal 1112 formed with foam, e.g., foam-filled cylinder or strip, that provides a foam seal or interface with the patient's mouth. A mount 1180 is provided to the mouth seal 1112 to support the mouth seal 1112 on a nasal mask. As illustrated, the mouth seal 1112 is shaped to fit the facial contours or profile of the patient's face.

Figure 28:
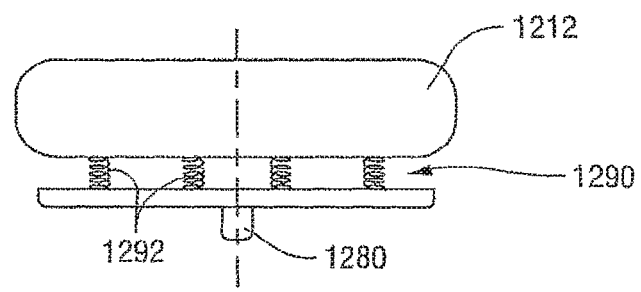

FIG. 28 illustrates a mouth seal 1212 formed with foam, e.g., foam-filled cylinder or strip, that provides a foam seal or interface with the patient's mouth. A mount 1280 is provided to the mouth seal 1212 to support the mouth seal 1212 on a nasal mask. As illustrated, a spring arrangement 1290, e.g., a plurality of coil springs 1292, is provided between the mount 1280 and the mouth seal 1212 to provide the mouth seal 1212 with a sealing force onto the patient's mouth. The sealing force provided by the spring arrangement 1290 will be opposed to the force of the air within the patient's mouth pressing against the lips.

Figure 29:
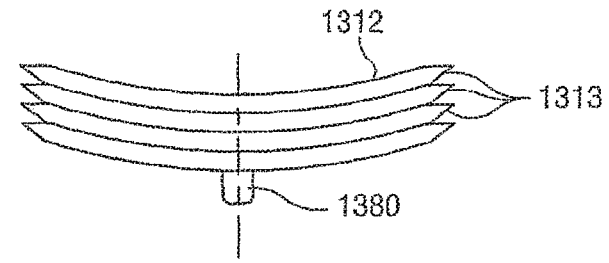

However, the sealing force may be generated by other suitable arrangements. For example, FIG. 29 illustrates a mouth seal 1312 including a concertina or bellows arrangement. A mount 1380 is provided to the mouth seal 1312 to support the mouth seal 1312 on a nasal mask. The plurality of bellows 1313 of the mouth seal 1312 provide the mouth seal 1312 with a sealing force onto the patient's mouth.

Figure 30:
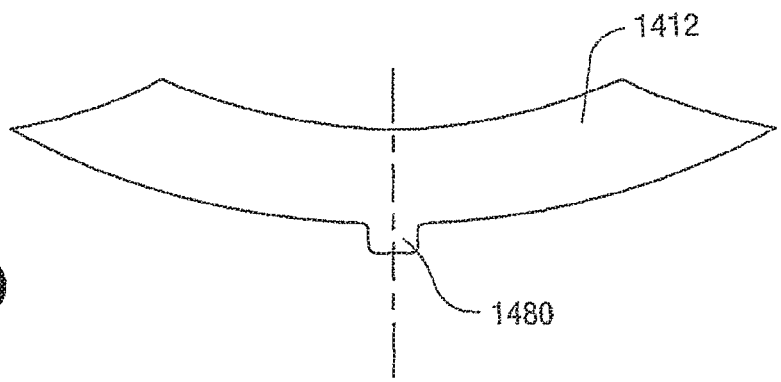

FIG. 30 illustrates a mouth seal 1412 including a gusset arrangement. A mount 1480 is provided to the mouth seal 1412 to support the mouth seal 1412 on a nasal mask. In use, pressurized air from the nasal mask is provided to the gusseted mouth seal 1412, e.g., via the mount 1480, to expand the gusseted mouth seal 1412 and provide a sealing force onto the patient's mouth.

In each of the above-described embodiments, the mouth sealing assembly 10, 210, 310, 410, 510, 610, 710, 810, 910 may be used as an optional component of a nasal mask system. That is, the mouth sealing assembly may be optionally used in conjunction with a nasal mask system to eliminate or at least minimize mouth leak in order to enhance the effectiveness of therapy.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mouth seal assembly for use with a nasal mask system, comprising:
    a mouth seal adapted to form a seal with the mouth of a patient, the mouth seal being substantially independent from a supply of pressurized air from the nasal mask system; and
    a mount provided to the mouth seal and adapted to support the mouth seal on the nasal mask system,
    wherein the mouth seal is formed with foam to provide a foam mouth seal with the patient's mouth in use, and
    wherein the mount is biased to provide the mouth seal with a sealing force onto the patient's mouth, the mouth seal assembly further comprising a spring arrangement between the mount and the mouth seal to provide the mouth seal with the sealing force.

2. The mouth seal assembly according to claim 1, wherein the foam mouth seal includes a foam-filled cylinder or strip.

3. The mouth seal assembly according to claim 1, further comprising an anti-asphyxia valve provided to the mouth seal over the patient's lips.

4. The mouth seal assembly according to claim 1, wherein the mouth seal is shaped or contoured to fit a facial profile around the patient's lips.

5. The mouth seal assembly according to claim 4, wherein the mouth seal includes upper and lower protrusions that define a space adapted to fit the patient's lips in use.

6. The mouth seal assembly according to claim 1, wherein the foam mouth seal is shaped to better fit the facial profile around the patient's lips.

7. The mouth seal assembly according to claim 1, wherein the mouth seal is adapted to form the seal with the patient's mouth when the patient's lips bellow outward due to pressurized air from the nasal mask system entering the patient's mouth.

8. The mouth seal assembly according to claim 1, wherein the mount is supported by one or more ports provided on the nasal mask system.

9. The mouth seal assembly according to claim 1, wherein the mount is supported by one or more headgear clips associated with headgear of the nasal mask system.

10. The mouth seal assembly according to claim 1, wherein the spring arrangement comprises coil springs or spring steel.

11. The mouth seal assembly according to claim 1, wherein the spring arrangement comprises a concertina or bellows arrangement.

12. A nasal mask system comprising:
    a nasal mask structured to form a seal with the nose of a patient and deliver a supply of pressurized air; and
    a mouth seal assembly according to claim 1.

13. A method of sealing the mouth of a patient, comprising:
    placing a mouth seal external to the mouth such that the mouth seal is not in a sealing relationship with the mouth;
    mounting the mouth seal on a mount being adapted to support the mouth seal on a nasal mask system,
    providing pressurized breathable gas to the patient using a nasal mask system;
    activating a seal between the patient's mouth and the mouth seal using the pressurized breathable gas; and
    biasing the mount with a spring arrangement to provide the mouth seal with a sealing force onto the patient's mouth.

14. The method of sealing the mouth of the patient according to claim 13, wherein the seal is activated by moving the patient's lips into sealing contact with the mouth seal by using the pressurized breathable gas.

15. The method of sealing the mouth of the patient according to claim 13, wherein the seal between the patient's mouth and the mouth seal is activated by mouth leak.

16. The method of sealing the mouth of the patient according to claim 13, wherein the seal between the patient's mouth and the mouth seal is activated by a differential pressure between the mouth and ambient.

17. The method of sealing the mouth of the patient according to claim 16, wherein the differential pressure causes the patient's lips to bellow into contact with the mouth seal.

18. The method of sealing the mouth of the patient according to claim 13, wherein the mouth seal comprises a substantially flat strip of material located external to and adjacent to the patient's lips.

19. The method of sealing the mouth of the patient according to claim 13, further comprising maintaining the mouth seal in place with a strap arrangement before and after the seal is activated.

20. The method of sealing the mouth of the patient according to claim 13, further comprising eliminating mouth leak as a result of the seal being activated.

21. The method of sealing the mouth of the patient according to claim 13, further comprising completely covering the mouth with the mouth seal.

22. The method of sealing the mouth of the patient according to claim 13, further comprising locating the mouth seal with a ridge on the mouth seal by placing the ridge between the patient's lips.

23. The method of sealing the mouth of the patient according to claim 13, further comprising sealing an anti-asphyxia valve in the mouth seal with the pressurized breathable gas.

24. The method of sealing the mouth of the patient according to claim 13, further comprising removing the pressurized breathable gas and allowing the patient to breathe freely though the mouth without having moved the mouth seal.

25. The method of sealing the mouth of the patient according to claim 13, wherein the spring arrangement comprises coil springs or spring steel.

26. The method of sealing the mouth of the patient according to claim 13, wherein the spring arrangement comprises a concertina or bellows arrangement.

\* \* \* \* \*